(12) United States Patent
Mott et al.

(10) Patent No.: US 8,521,439 B2
(45) Date of Patent: Aug. 27, 2013

(54) METHOD OF USING A CALIBRATION SYSTEM TO GENERATE A LATENCY VALUE

(75) Inventors: Christopher Grey Mott, Vancouver (CA); Daniel Joseph Mollicone, Philadelphia, PA (US)

(73) Assignee: Pulsar Informatics, Inc., Philadelphia, PA (US)

( * ) Notice: Subject to any disclaimer, the term of this patent is extended or adjusted under 35 U.S.C. 154(b) by 376 days.

(21) Appl. No.: 12/777,107

(22) Filed: May 10, 2010

(65) Prior Publication Data

US 2010/0312508 A1    Dec. 9, 2010

Related U.S. Application Data

(60) Provisional application No. 61/215,728, filed on May 8, 2009.

(51) Int. Cl.
G01N 33/48    (2006.01)
(52) U.S. Cl.
USPC .......................................................... 702/19
(58) Field of Classification Search
None
See application file for complete search history.

(56) References Cited

U.S. PATENT DOCUMENTS

| | | | |
|---|---|---|---|
| 4,038,561 A | 7/1977 | Lorenz | |
| 4,228,806 A | 10/1980 | Lidow | |
| 4,234,944 A | 11/1980 | Komaki et al. | |
| 4,670,864 A | 6/1987 | Hoffman | |
| 4,724,378 A | 2/1988 | Murray et al. | |
| 4,894,813 A | 1/1990 | Pacher et al. | |
| 4,926,969 A * | 5/1990 | Wright et al. | 600/544 |
| 5,006,985 A | 4/1991 | Ehret et al. | |
| 5,101,831 A | 4/1992 | Koyama et al. | |
| 5,140,562 A | 8/1992 | Moore-Ed et al. | |
| 5,163,426 A | 11/1992 | Czeisler et al. | |
| 5,167,228 A | 12/1992 | Czeisler et al. | |
| 5,176,133 A | 1/1993 | Czeisler et al. | |
| 5,197,941 A | 3/1993 | Whitaker | |
| 5,212,672 A | 5/1993 | Loisch et al. | |
| 5,304,212 A | 4/1994 | Czeisler et al. | |
| 5,343,121 A | 8/1994 | Terman et al. | |
| 5,433,223 A | 7/1995 | Moore-Ede et al. | |
| 5,524,101 A | 6/1996 | Thorgersen et al. | |
| 5,545,192 A | 8/1996 | Czeisler et al. | |
| 5,589,741 A | 12/1996 | Terman et al. | |
| 5,846,206 A | 12/1998 | Bader | |
| 5,928,133 A | 7/1999 | Halyak | |
| 6,070,098 A | 5/2000 | Moore-Ede et al. | |
| 6,236,622 B1 | 5/2001 | Blackman | |
| 6,241,686 B1 | 6/2001 | Balkin et al. | |
| 6,350,275 B1 | 2/2002 | Vreman et al. | |
| 6,419,629 B1 | 7/2002 | Balkin et al. | |
| 6,527,715 B2 | 3/2003 | Balkin et al. | |
| 6,553,252 B2 | 4/2003 | Balkin et al. | |
| 6,579,233 B2 | 6/2003 | Hursh | |
| 6,712,615 B2 | 3/2004 | Martin | |
| 6,740,032 B2 | 5/2004 | Balkin et al. | |
| 6,743,167 B2 | 6/2004 | Balkin et al. | |
| 6,842,737 B1 | 1/2005 | Stiles et al. | |
| 6,894,606 B2 | 5/2005 | Forbes et al. | |
| 7,085,726 B1 | 8/2006 | Galperin et al. | |
| 7,207,938 B2 | 4/2007 | Hursh | |
| 7,672,802 B2 | 3/2010 | Foreman | |
| 2003/0013943 A1 | 1/2003 | Hursh | |
| 2005/0015122 A1 | 1/2005 | Mott et al. | |
| 2005/0105682 A1 | 5/2005 | Heumann et al. | |

FOREIGN PATENT DOCUMENTS

| | | |
|---|---|---|
| CA | 2439938 | 9/2002 |
| CA | 2599984 | 9/2006 |
| FR | 2893245 | 5/2007 |
| JP | 2007044203 | 2/2004 |

OTHER PUBLICATIONS

Kim, H. et al., "Sleep-Disordered Breathing and Psychomotor Vigilance in a Community-Based Sample", Sleep, vol. 30, No. 10, 2007, pp. 1309-1316.
Kribbs, N. et al., "Effects of One Night without Nasal CPAP Treatment on Sleep and Sleepiness in Patients with Obstructive Sleep Apnea", Am Rev Dis, vol. 147, 1993, pp. 1162-1168.
Lim, J. et al., "Sleep Deprivation and Vigilant Attention", Annals of the New York Academy of Sciences 1129, 2008, pp. 305-322.
Lim, J. et al., "Imaging brain fatigue from sustained mental workload: ASL perfusion study of the time-on-task effect", NeuroImage 49, 2010, pp. 3426-3435.
Lim, J. et al., "Sleep Deprivation Impairs Object-Selective Attention: A View from the Ventral Visual Cortex", PLoS One www.plosone.org, Feb. 2010, vol. 5, Issue 2, e9087, pp. 1-9.
Lim, J. et al., "A Meta-Analysis of the Impact of Short-Term Sleep Deprivation on Cognitive Variables", Psychological Bulletin, vol. 136, No. 3, 2010, pp. 375-389.
Luik, A. et al., "Inter-Individual Differences in Performance on a Letter Verbal Fluency Task During Sleep Deprivation", NSWO 19, 2008, pp. 105-108.
Maislin, G. et al., "A Survey Screen for Prediction of Apnea", Sleep, vol. 18, No. 3, 1995, pp. 158-166.

(Continued)

*Primary Examiner* — Pablo S Whaley
(74) *Attorney, Agent, or Firm* — Todd A. Rattray, Esq.; Damian M. Biondo, Esq.

(57) ABSTRACT

Methods are provided for calibrating stimulus-response test systems which include a stimulus output device for delivering a stimulus to a subject; and a response input device for receiving a response from the subject. One such method comprises: sensing the stimulus event output by the stimulus output device; recording a calibrator stimulus time associated with detection of the stimulus event in a calibrator separate from the stimulus-response test system; generating a calibrator response after sensing the stimulus event, the calibrator response causing a response input port of the stimulus-response test system to receive a calibrator response signal and to deliver a corresponding calibrator response signal to the test controller; recording a calibrator response time associated with generation of the calibrator response in the calibrator; and determining a latency value associated with the stimulus-response test system based at least in part on a difference between the calibrator response time and the calibrator stimulus time.

12 Claims, 10 Drawing Sheets

(56) References Cited

OTHER PUBLICATIONS

Mallis, M. et al., "Summary of the Key Features of Seven Biomathematical Models of Human Fatigue and Performance", Aviation, Space, and Environment Medicne, vol. 75, No. 3, Section II, Mar. 2004, pp. A4-A14.

McCauley, P. et al., "A new mathematical model for the homeostatic effects of sleep loss in neurobehavioral performance", Journal of Theoretical Biology 256, 2009, pp. 227-239.

Mitler, M. et al., "Catastrophes, Sleep, and Public Policy: Consensus Report", Sleep, vol. 11, No. 1, 1988, pp. 100-109.

Moest, E., "On the relationship between inter-individual differences in performance impairment from sleep loss and inter-individual differences in sleep architecture", 2003, pp. 55-58.

Mollicone, D. et al., "Optimizing sleep/wake schedules in space: Sleep during chronic nocturnal sleep restriction with and without diurnal naps", Acta Astronautica, vol. 60, 2007, p. 354-361.

Mollicone, D. et al., "Response surface mapping of neurobehavioral performance: Testing the feasibility of split sleep schedules for space operations", Acta Astronautica, vol. 63, 2008, pp. 833-840.

Mollicone, D. et al., "Time of day effects on Neurobehavioral performance during chronic sleep restriction", Aviation, Space, and Environmental Medicine, vol. 81, No. 1, Aug. 2010, pp. 735-744.

Mullington, J. et al., "Sleep loss reduces diurnal rhythm amplitude of leptin in healthy men", Journal of Neuroendocrinology, vol. 15, 2003, pp. 851-854.

Neri, D. et al., "Controlled Breaks as a Fatigue Countermeasure on the Flight Deck", Aviation, Space, and Environmental Medicine, vol. 73, No. 7, Jul. 2002, pp. 654-664.

Olofsen, D. et al., "Nonlinear Mixed-Effects Modeling: Individualization and Prediction", Aviation, Space, and Environmental Medicine, vol. 75, No. 3, Section II, Mar. 2004, pp. A134-A140.

Pack, A. et al., "Characteristics of crashes attributed to the driver having fallen asleep", Accid. Anal. and Prev., vol. 27, No. 6, 1995, pp. 769-775.

Pack, A. et al., "Impaired performance in commercial drivers: Role of sleep apnea and short sleep duration", Am J Respir Crit Care Med, vol. 174, 2006, pp. 446-454.

Pakola, S. et al., "Driving and Sleepiness: Review and regulations and guidelines for commercial and noncommercial drivers with sleep apnea and narcolepsy", Sleep, vol. 18, No. 9, 1995, pp. 787-796.

Powell, N. et al., "A Comparative Model: Reaction Time Performance in Sleep-Disordered Breathing Versus Alcohol-Impaired Controls", The Larynoscope, vol. 109, Oct. 1999, pp. 1648-1654.

Rangan, S., "Integrated Fatigue Modeling in Crew Rostering and Operations", Fedex Express Flight Operations, 2011, pp. 1-10.

Rogers, N. et al., "Shiftwork, Circadian Disruption and Consequences", Clinical Focus, Primary Psychiatry, vol. 9, No. 8, Aug. 2002, pp. 50-56.

Rogers, N. et al., "Potential Action of Melatonin in Insomnia", Sleep, vol. 26, No. 8, 2003, pp. 1058-1059.

Rogers, A. et al., "The Working Hours of Hospital Staff Nurses and Patient Safety", Health Affairs, vol. 23, No. 4, Jul./Aug. 2004, pp. 202-212.

Rogers, N. et al., "Caffeine: Implications for Alertness in Athletes", Clinics in Sports Medicine, vol. 24, 2005, pp. e1-e13.

Rogers, N. et al., "Interaction of chronic sleep restriction and circadian system in humans", J. Sleep Res., 2008, pp. 1-6.

Rosekind, M. et al., "From Laboratory to Flightdeck: Promoting Operational Alertness", The Royal Aeronautical Society, 1997, pp. 7.1-7.14.

Scott, L. et al., "The Relationship between Nurse Work Schedules, Sleep Duration, and Drowsy Driving", Sleep, vol. 30, No. 12, 2007, pp. 1801-1807.

Smith-Coggins, R. et al., "Rotating Shiftwork Schedules: Can We Enhance Physician Adaptation to Night Shifts?", Acad. Emerg. Med., vol. 4, 1997, pp. 951-961.

Stakofsky, A.B. et al., "Candidate Predictions of Vulnerability to Sleep Deprivation", 2004, p. 80-83.

Tucker, A. et al., "Trait interindividual differences in the sleep physiology of healthy young adults", J. Sleep Res., vol. 16, 2007, pp. 170-180.

Van Dongen, H. et al., "Circadian phase delay during 88-hour sleep deprivation in dim light: differences among body temperature, plasma melatonin and plasma cortisol", 2000, pp. 33-36.

Van Dongen, H. et al., "Caffeine eliminates sleep inertia after awakening from reduced sleep", 2000, pp. 1-23.

Van Dongen, H. et al., "A mixed regression model of cumulative sleep debt in chronic sleep restriction", Sleep-Wake, Research in the Netherlands, vol. 12, 2001, pp. 31-33.

Van Dongen, H. et al., "Investigating the interaction between the homeostatic and circadian processes of sleep-wake regulation for the prediction of waking neurobehavioural performance", J. Sleep Res., vol. 12, 2003, pp. 181-187.

Van Dongen, H. et al., "The Cumulative Cost of Additional Wakefulness: Dose-Response Effects on Neurobehavioral Functions and Sleep Physiology From Chronic Sleep Restriction and Total Sleep Deprivation", Sleep, vol. 26, No. 2, 2003, pp. 117-126.

Van Dongen, H. et al., "Sleep debt: Theoretical and empirical issues", Sleep and Biological Rhythms, vol. 1, 2003, pp. 5-13.

Van Dongen, H. et al., "Systematic Interindividual Differences in Neurobehavioral Impairment from Sleep Loss: Evidence of Trait-Like Differential Vulnerability", Sleep, vol. 27, No. 3, 2004, pp. 423-433.

Van Dongen, H. et al., "Circadian Rhythms in Sleepiness, Alertness, and Performance", Chronobiology, 2005, pp. 435-443.

Van Dongen, H. et al., "Sleep, Circadian Rhythms, and Psychomotor Vigilance", Clinics in Sports Medicine, vol. 24, 2005, pp. 237-249.

Van Dongen, H. et al., "Optimization of Biomathematical Model Predictions for Cognitive Performance Impairment in Individuals: Accounting for Unknown Traits and Uncertain States in Homeostatic and Circadian Processes", Sleep, vol. 30, No. 9, 2007, pp. 1129-1143.

Van Dongen, H. et al., "The Efficacy of a Restart Break for Recycling with Optimal Performance Depends Critically on Circadian Timing", Sleep, vol. 34, No. 7, 2011, pp. 1-13.

Varkevisser, M. et al., "Physiological Indices in Chronic Insomnia During a Constant Routine: The Role of Hyperarousal", 2004, pp. 96-99.

Varkevisser, M. et al., "Chronic Insomnia and Ambulatory Daytime Functioning", NSWO, vol. 16, 2005, pp. 171-176.

Vitellaro, A. et al., "Neurobehavioral Performance Under Varying Workload Conditions During Repeated Exposure to Sleep Deprivation", 2003, pp. 106-109.

Weaver, T. et al., "Night-To-Night Variability in CPAP Use Over the First Three Months of Treatment", Sleep, vol. 20, No. 4, 1997, pp. 278-283.

Weaver, T. et al., "An Instrument to Measure Functional Status Outcomes for Disorders of Excessive Sleepiness", Sleep, vol. 20, No. 10, 1997, pp. 835-843.

Weaver, T. et al., "Self-Efficacy in Sleep Apnea: Instrument Development and Patient Perceptions of Obstructive Sleep Apnea Risk, Treatment Benefit, and Volition to Use Continuous Positive Airway Pressure", Sleep, vol. 26, No. 6, 2003, pp. 727-732.

Letter from The Black Box ToolKit to Chernoff, Vilhauer, McClung & Stenzel, LLP, dated Jan. 17, 2012, 2 pgs.

The Black Box ToolKit User Guide, by Dr. Richard R. Plant, 2004, pp. cover, 2-4, 14-22, 35-40, 47-50, 72, 87 and 91.

Richard R. Plant et al., "Toward an Experimental Timing Standards Lab: Benchmarking precision in the real world," Behavior Research Methods, Instruments & Computers, 2002, 34(2), pp. 218-226.

Richard R. Plant et al., "How choice of mouse may affect response timing in psychological studies," Behavior Research Methods, Instruments & Computers, 2003, 35(2), pp. 276-2846.

Richard R. Plant et al., "Self-validating presentation and response timing in cognitive paradigms: How and why?," Behavior Research Methods, Instruments & Computers, 2004, 36(2), pp. 291-303.

Kenneth I. Forster et al., "DMDX: A Windows display program with millisecond accuracy," Behavior Research Methods, Instruments & Computers, 2003, 35(1), pp. 116-124.

Weaver, T. et al., "Relationship Between Hours of CPAP Use and Achieving Normal Levels of Sleepiness and Daily Functioning", Sleep, vol. 30, No. 6, 2007, pp. 711-719.

Webber, M. et al., "Introversion, Type A Personality, and Resilience to Cognitive Impairrment from Sleep Loss", NSWO, vol. 18, 2007, pp. 131-134.
The Black Box Toolkit, Ltd., "The Black Box Toolkit: User's Guide" (unedited version), Black Box Toolkit, Ltd. 2004. (complete version, including Chapter 7 on "Calibration").
Avinash, D. et al., "Parameter Estimation for a Biomathematical Model of Psychomotor Vigilance Performance Under Laboratory Conditions of Chronic Sleep Restriction", Sleep-Wake: Research in the Netherlands, vol. 16, 2005, pp. 39-42.
Banks, S. et al., "Behavioral and Physiological Consequences of Sleep Restriction", Journal of Clinical Sleep Medicine, 2007, pp. 519-528.
Banks, S. et al., "Neurobehavioral Dynamics Following Chronic Sleep Restriction: Dose-Response Effects of One Night for Recovery", Sleep, vol. 33, No. 8, 2010, pp. 1013-1026 & S1-S3.
Basner, M. et al., "Effects of Night Work, Sleep Loss and Time on Task on Simulated Threat Detection Performance", Sleep, vol. 31, No. 9, 2008, pp. 1251-1259.
Basner, M. et al., "American Time Use Survey: Sleep Time and Its Relationship to Waking Activities", Sleep, vol. 30, No. 9, 2007, pp. 1085-1095.
Basner, M. et. al., "Dubious Bargain: Trading Sleep for Leno & Letterman", Sleep, vol. 32., No. 6, 2009, pp. 747-752.
Baynard, M. et. al., "Systematic Inter-Individual Differences in Sleep Stage Percentages", 2004, pp. 16-18.
Blaauw, M. et. al., "Trait-like Inter-individual Differences in Sleep Cycle Duration", 2002, p. 16-19.
Buysse et. al., "Sleep, Fatigue, and Medical Training: Setting and Agenda for Optimal Learning and Patient Care", Sleep, vol. 26, No. 2, 2003, pp. 218-225.
Chaumet, G. et. al., "Confinement and Sleep Deprivation Effects on Propensity to Take Risks", Aviation, Space, and Environmental Medicine, vol. 80, No. 2, Feb. 2009, pp. 73-80.
Chee, M. et. al., "Functional imaging of working memory following normal sleep and after 24 and 35 h of sleep deprivation: Corelations of fronto-parietal activation and performance", NeuroImage 31, 2006, pp. 419-428.
Chee, M. et. al., "Lapsing during Sleep Deprivation Is Associated with Distributed Changes in Brain Activation", The Journal of Neuroscience, May 21, 2008, pp. 5519-5528.
Chugh, D. et al., "Neurobehavioral Consequences of Arousals", Sleep, vol. 19, No. 10, 1996, pp. 000-000.
Czeisler, C. et al., "Modafinil for Excessive Sleepiness Associated with Shift-Work Sleep Disorder", The New England Journal of Medicine, Aug. 4, 2005, pp. 476-486.
Dinges, David F., "The Nature and Timing of Sleep", Transitions & Studies of the College of Physicians of Philidelphie, Ser. 5, vol. 6, No. 3 (1984), pp. 177-206.
Dinges, D. et al., "Assessing performance upon abrupt awakening from naps during quasi-continuous operations", Behavior Research Methods, Instruments, & Computers, 1985, pp. 37-45.
Dinges, D. et al., "Microcomputer analyses of performance on a portable, simple visual RT task during sustained operations", Behavior Research Methods, Instruments, & Computers, 1985, pp. 652-655.
Dinges, D. et al., "Napping to Sustain Performance and Mood: Effect of Circadian Phase and Sleep Loss", paper presented at The Seventh International Symposium on Night-and Shiftwork, Sep. 18-21, 1985, Austria.
Dinges, David F., "Differential Effects of Prior Wakefulness and Circadian Phase on Nap Sleep", Electroencephalography and Clinical Neurophysiology, 1986, pp. 224-227.
Dinges, D. et al., "Temporal Placement of Nap for Alertness: Contributions of Circadian Phase and Prior Wakefulness", Sleep, 10(4), 1987, pp. 313-329.
Dinges, D. et al., "The benifits of a nap during prolonged work and wakefulness", Work & Stress, 1988, vol. 2, No. 2, pp. 139-153.
Dinges, D. et al., "Comparison of the Effects of Alcohol and Sleepiness on Simple Reaction Time Performance: Enhanced Habituation as a Common Process", Alcohol, Drugs and Driving, 1990, vol. 5, No. 4/vol. 6, No. 1, pp. 1-11.

Dinges, David F., "An overview of sleepiness and accidents", European Sleep Research Society, 1995, pp. 4-14.
Dinges, D. et al., "Cumulative Sleepiness, Mood Disturbance, and Psychomotor Vigilance Performance Decrements During a Week of Sleep Restricted to 4-5 Hours per Night", Sleep, 1997, pp. 264-277.
Dinges, D. et al., "Future Considerations for Models of Human Neurobehavioral Function", Journal of Biological Rhythms, vol. 14, No. 6, Dec. 1999, pp. 121-124.
Dinges, D. et al., "Recognizing Problem Sleepiness in Your Patients", American Family Physician, Feb. 15, 1999, Web Archive.
Dinges, D. et al., "Cumulative Sleep Loss in Space Flight: Neurobehavioral Consequences and Countermeasures", International Astronautical Federation, 2001, pp. 1-7.
Dinges, D. et al. "Effects of modafinil on sustained attention performance and quality of life in OSA patients with residual sleepines while being treated with nCPAP", Sleep Medicine, Mar. 28, 2003, pp. 1-10.
Dinges, David F., "Critical Research Issues in Development of Biomathematical Models of Fatigue and Performance", Aviation, Space, and Environmental Medicine, vol. 75, No. 3, Section II, Mar. 2004, pp. A181-A191.
Dinges, D. et al., "Pilot Test of Fatigue Management Techniques", TRB 2005 Annual Meeting, Paper # 05-1234.
Dinges, David F., "Cocoa Flavanols, Cerebral Blood Flow, Cognition, and Health: Going Forward", J Cardiovasc Pharmacol, vol. 00, No. 00, 2006, Article No. 200260, pp. 1-3.
Dinges, D. et al., "Pharmacodynamic effects on alertness of single doses of armodafinil in healthy subjects during a nocturnal period of acute sleep loss", Current Medical Research and Opinions, vol. 22, No. 1, 2006, pp. 159-167.
Dinges, D. et al., "Monitoring of Facial Stress during Space Flight: Optical Computer Recognition Combining Discriminative and Generative Methods", 2007, pp. 1-27.
Doran, S.M. et al., "Sustained Attention Performance During Sleep Deprivation: Evidence of State Instability", Archives Italiennes De Biologie, 139, 2001, pp. 253-267.
Drummond, S. et al., "The Neural Basis of Psychomotor Vigilance Task", Sleep, vol. 28, No. 9, 2005, pp. 1059-1068.
Durmer, J. et al., "Neurocognitive Consequences of Sleep Deprivation", Seminars in Neurology, vol. 25, No. 1, 2005, pp. 117-129.
Findley, L. et al., "Time-on-task Decrements in "Steer Clear" Performance of Patients with Sleep Apnea and Narcolepsy", Sleep, Vo. 22, No. 6, 1999, pp. 804-809.
Goel, N. et al., "Neurocognitive Consequences of Sleep Deprivation", Semin Neurol, 2009, pp. 320-339.
Goel, N. et al., "PER3 Polymorphism Predicts Cumulative Sleep Homeostatic but Not Neurobehavioral Changes to Chronic Partial Sleep Deprivation", PLoS One www.plosone.org, Jun. 2009, vol. 4, Issue 6, pp. 1-13.
Gooneratne, N., et al., "Consequences of Comorbid Insomnia Symptoms and Sleep-Related Breathing Disorder in Elderly Subjects", Arch Intern Med., vol. 166, Sep. 18, 2006, pp. 1732-1738.
Grace, R. et al., "The Carnege Mellon Trucksim: A Tool to Improve Driving Safety", IEEE, 0-7803-5086-3, 1998, pp. 135-1-135-8.
Gross, J. et al., "Computational Modeling of the Combined Effects of Circadian Rhythm and Sleep Deprivation", 2006, pp. 297-302.
Gunzelmann, G. et al., "A Neurobehaviorally Inspired ACT-R Model of Sleep Deprivation: Decreased Performance in Psychomotor Vigilance", pp. 857-862, (2005).
Gunzelmann, G. et al., "Understanding Decrements in Knowledge Access Resulting from Increased Fatigue", Proceedings of the Twenty-Ninth Annual Meeting of the Cognitive Science Society, 2007, pp. 329-334.
Gunzelmann, G. et al., "Individual Differences in Sustained Vigilant Attention: Insights from Computational Cognitive Modeling", Proceedings of the Thirtieth Annual Meeting of the Cognitive Science Society, 2008, pp. 2017-2022.
Gunzelmann, G. et al., "Examining Sources of Individual Variation in Sustained Attention", 2009, pp. 608-613.
Gunzelmann, G. et al., "Sleep Deprivation and Sustained Attention Performance: Integrating Mathematical and Cognitive Modeling", Cognitive Science 33, 2009, pp. 880-910.

Hoffman, J. et al., "Time of Day and Sleep Inertia Effects on Cognitive Performance and Sleepiness During Chronic Sleep Restriction", NSWO 16, 2005, pp. 75-78.

Jewett, M. et al., "Dose-response Relationship Between Sleep Duration and Human Psychomotor Vigilance and Subjective Alertness", Sleep, vol. 22, No. 2, 1999, pp. 171-179.

Kelly, S. et al., "Flight Controller Alertness and Performance During Spaceflight Shiftwork Operations", The Society for Human Performance in Extreme Environments (HPEE), vol. 3, No. 1, Sep. 1998, pp. 100-106.

Van Dongen, H.P.A. et al., "Optimization of biomathematical model predictions for cognitive performance impairment in individuals: accounting for unknown traits and uncertain states in homeostatic and circadian processes", Sleep, vol. 30, No. 9, Sep. 2007, pp. 1129-1143.

Kronauer, R.E., et al., "Uncovering physiological mechanisms of circadian rhythms and sleep/wake regulation through mathematical modeling", Journal of Biological Rhythms, vol. 22, No. 3, Jun. 2007, pp. 233-245.

Czeisler et al.; Stability, Precision, and Near-24-Hour Period of the Human Circadian Pacemaker; Science, vol. 284, No. 5423 (1999), pp. 2177-2181.

Czeisler et al.; Bright Light Resets the Human Circadian Pacemaker Independent of the Timing of the Sleep-Wake Cycle; Science, vol. 233, No. 4764 (Aug. 1986), pp. 667-671.

Jewett et al.; Revised Limit Cycle Oscillator Model of Human Circadian Pacemaker; Journal of Biological Rhythms, vol. 14, No. 6 (1999), pp. 493-499.

Jewett et al.; Phase-Amplitude Resetting of the Human Circadian Pacemaker via Bright Light: A Further Analysis; Journal of Biological Rhythms, vol. 9, Nos. 3-4(1994), pp. 295-314.

Czeisler et al.; Entrainment of Human Circadian Rhythms by Light-Dark Cycles: A Reassessment; Photochemistry and Photobiology, vol. 34, No. 2 (Aug. 1981), pp. 239-247.

Huzmezan et al.;Reconfigurable Flight Control of a High Incidence Research Model . . . ;UKACC Intl. Conf. on Control '98,Sep. 1-4, 1998,Conf. publ. No. 455,IEE 1998, pp. 1169-1174.

Jewett et al; Light-Induced Suppression of Endogenous Circadian Amplitude in Humans; Nature, vol. 350, No. 6313 (Mar. 1991), pp. 59-62.

Khalsa et al.; The Timing of the Human Circadian Clock is Accurately Represented by the Core Body . . . ; Journal of Biological Rhythms, vol. 15, No. 6 (Dec. 2000), pp. 524-530.

Kronauer et al.;Mathematical Model of the Human Circadian System with Two Interacting Oscillators; American Journal of Physiology; vol. 242, No. 1 (Jan. 1982), pp. R3-R17.

Shanahan et al.; Melatonin Rhythm Observed Throughout a Three-Cycle Bright-Light Stimulas . . . ; Journal of Biological Rhythms, vol. 14, No. 3 (Jun. 1999), pp. 237-253.

Wyatt et al.; Circadian Temperature and Melatonin Rhythms, Sleep and Neurobehavioral . . . ; American Journal of Physiology, vol. 277, No. 4 (Oct. 1999), pp. R1152-R1163.

Waterhouse et al.; Estimates of the Daily Phase and Amplitude of the Endogenous Component of the Circadian . . . ; Biological Rhythm Research 2000, vol. 31, No. 1, pp. 88-107.

Richard E. Kronauer; A Model for the Effect of Light on the Human "Deep" Circadian Pacemaker; Sleep Research, 16(621), 1987.

MBI Pulsar Presentation, Oct. 27, 2006.

Mott, Christopher et al., "Modifying Circadian Pacemaker Using Model Based Predictive Control," Proceedings of the 2003 American Control Conference, Denver, Colorado, Jun. 4, 2003, pp. 453-458.

Measuring Light Intensity, Reference Note 50, D.R. Wulfingoff 1999.

www.cybercollege.com/tvp029.htm, Dec. 26, 2003, Module 29 "Light Intensity".

Rawlings, James B., "Tutorial: Model Predictive Control Technology," Proceedings of the American Control Conference, San Diego, California, Jun. 2009, pp. 662-676.

Van Dongen, H.P.A. et al., "Mixed-Model Regression Analysis and Dealing with Interindividual Differences," Methods in Enzymology, vol. 384, pp. 139-171, (2004).

Olofsen, Erik et al., "Population Pharmacokinetics/Pharmacodynamics of Anesthetics," The AAPS Journal 2005; 7 (2) Article 39, pp. E238-E389.

Minto, Charles et al., "Expanding clinical applications of population pharmacodynamic modelling," Br J Clin Pharmacol 1998; 46: 321-333.

Van Dongen, H.P.A. et al., "Dealing with Inter-Individual Differences in the Temporal Dynamics of Fatigue and Performance: Importance and Techniques," Aviation, Space, and Environmental Medicine; vol. 75, No. 3, Section II, Mar. 2004, pp. A147-A154.

Olofsen, Erik et al., "Nonlinear Mixed-Effects Modeling: Individualization and Prediction," Aviation, Space, and Environmental Medicine; vol. 75, No. 3. Section II, Mar. 2004.

Jonsson, E.N. et al., "Nonlinearity Detection: Advantages of Nonlinear Mixed-Effects Modeling," AAPS PharmSci 2000; 2(3) article 32, pp. 1-10.

Gentilini, Andrea et al., "Multitasked Closed-Loop Control in Anesthesia," IEEE Engineering in Medicine and Biology, Jan./Feb. 2001, pp. 39-53.

Doufas, Anthony G. et al., "Induction Speed Is Not a Determinant of Propofol Pharmacodynamics," Anesthesiology, V 101, No. 5, Nov. 2004, pp. 1112-1121.

Dinges, David F., "Critical Research Issues in Development of Biomathematical Models of Fatigue and Performance," Aviation, Space, and Environmental Medicine, vol. 75, No. 3, Section II, Mar. 2004, pp. A181-A191.

Ihler, A., "Kernel density estimation toolbox for MATLAB," http//www.ics.uci.edu/ihler/code/kde.html, 2003.

Morari et al., "Model Predictive Control Toolbox for Use with MATLAB", Oct. 1998.

* cited by examiner

METHOD OF USING A CALIBRATION SYSTEM TO GENERATE A LATENCY VALUE

RELATED APPLICATIONS

This application claims the benefit of the priority of U.S. application No. 61/215,728, filed 8 May 2009 which is hereby incorporated herein by reference.

TECHNICAL FIELD

The invention relates to stimulus-response testing performed on humans or other animals. Particular embodiments provided methods and systems for calibration of stimulus-response testing systems.

BACKGROUND

Stimulus-response tests include a wide variety of tests which may be used to evaluate, inter alia, cognitive and neurobehavioural performance of human and other animal subjects. Non-limiting examples of stimulus-response tests include: psychomotor vigilance task (PVT) tests, digit symbol substitution task (DSST) tests, stroop tests and/or the like.

In general, stimulus-response tests involve providing stimulus to a subject (e.g. a human or other animal subject) and observing the resultant response. Observed responses may then be further analyzed. Analysis of results from stimulus-response tests may include generating metrics indicative of the type of response (e.g. for a given stimulus event) and/or the timing of the response (e.g. relative to the timing of a stimulus event). It will be appreciated that for stimulus-response tests, where the timing of the response relative to the stimulus is considered to be important, measurement of the timing of stimulus and response events may be of commensurate importance.

In many cases, stimulus-response tests are conducted using a general purpose computer which may be outfitted with a suitable stimulus output device and a suitable response input device. FIG. 1 is a schematic block diagram illustration of a particular exemplary stimulus-response test delivery system 100 implemented on a general purpose computer 102 wherein the test is being administered on a subject 104. In addition to computer 102, test delivery system 100 incorporates a stimulus output device 106 for providing a stimulus output 108 to subject 104 and a response input device 119 for receiving a response 112 from subject 104. Stimulus output device 106 may comprise a well known computer output device (e.g. a monitor, speakers or the like) or may comprise a specialized output device (e.g. digitally controlled light source or the like) for the purpose of implementing a particular stimulus-response test. Similarly, response input device 110 may comprise a well known computer input device (e.g. a mouse, a keyboard, a touch screen, a graphics tablet or the like) or a specialized input device (e.g. a button, a digital audio input device (e.g. microphone), a still camera, a video camera, a force-feedback device or the like).

Computer 102 includes a controller 114 (e.g. a CPU or the like). Controller 102 typically has access to a hard drive 116 and/or other memory (e.g. RAM memory) 118, which houses a number of software applications 120A ... 120i (collectively, software applications 120) or suitable portions of such software applications 120. Typically, software applications 120 will reside at least in part on hard drive 116 and may be loaded into memory 118 in whole or in part, as and when required by controller 114. As is known, controller 114 may multi-task in order to run a relatively large number of software applications 120 at the same time. One or more of software applications 120 may include the software application(s) associated with the administration of the stimulus-response test. Other software applications 120 may include, by way of non-limiting example, the operating system associated with computer 102, drivers associated with I/O interfaces 130 and I/O devices 132, any other programs which a test administrator may be running on computer 102 and/or the like.

Computer 102 also typically includes a stimulus output interface 122 which sends appropriate output signals 124 to stimulus output device 106 under the direction of controller 114 (e.g. via signal 115). By way of non-limiting example, stimulus output interface 122 can comprise any I/O interface common to computers, such as a USB port, a serial port, a parallel port, a network port (e.g. a wireless network port, an ethernet port), a IEEE 1394 interface (e.g. FireWire™) port or the like. Stimulus output interface 122 may be physically connected to deliver signal 124 to stimulus output device 106 or wirelessly connected to deliver signal 124 to stimulus output device 106. Computer 102 also typically includes a response input interface 126 which receives response signal 128 from response input device 110 and relays this information to controller 114 (e.g. via test-system response signal 127). Response input interface 126 may comprise any of the non-limiting exemplary interfaces described above for stimulus output interface 122. Response input interface 126 may be physically connected to receive response signal 128 from response input device 110 or wirelessly connected to receive response signal 128 from response input device 110. In addition to stimulus output interface 122 and response input interface 126, computer 102 may include other I/O interfaces 130 which interface with other I/O devices 132 under the direction of controller 114.

In operation, controller 114 runs one or more software applications 120 associated with the administration of the stimulus-response test and outputs a suitable signal 115 which causes stimulus output interface 122 to output signal 124 and stimulus output device 106 to output a stimulus event 108. When subject 104 perceives stimulus event 108 to be of the type for which a response is desired, subject 104 responds 112 using response input device 110 which generates a response signal 128 at response input interface 126 which is then directed to controller 114 as test-system response signal 127. An issue, particularly when the timing of response 112 relative to stimulus event 108 is of interest is the latency associated with computer 102, the latency of the response input device 110, the latency of the stimulus output device 106, and the latency of the interfaces between these components (e.g. response input interface 126 and stimulus output interface 122). By way of non-limiting example, computer 102 may exhibit latency because of processing delays (e.g. processor 114 is busy performing the processing associated with one or more of software applications 120), because of delays associated with the interfacing between controller 114 and memory 118, between controller 114 and hard drive 116 and/or between hard drive 116 and memory 118, because of delays associated with interfacing between I/O interfaces 122, 126, 130 and/or I/O devices 106, 110, 132 and/or the like. By way of non-limiting example, stimulus output device 106 may exhibit latency between receiving an output signal 124 and transmitting stimulus 108 due to processing delays associated with stimulus output device 106, mechanical delays (e.g. switch turning on), optical displays transitioning between on and off states (e.g. pixels on an LCD monitor) and/or the like. By way of non-limiting example response input device 110 may exhibit latency between receiving response 112 and transmitting response signal 128 due to processing delays in the response input device 110, mechanical delays (e.g. travel time of a button before electrical connection is made), electrical delays (e.g. debouncing circuits, or time for signal to cross a detection threshold) and/or the like. Such latencies can easily be on the order of magnitude of the stimulus-response timing for which a measurement is desired.

There is a general desire to provide systems and methods for calibrating a stimulus-response test delivery system to account for such latency. Such calibration may permit the timing metrics associated with stimulus-response tests to be determined with increased accuracy and/or precision and/or may provide more information about the certainty/confidence associated with stimulus-response test results.

It can be desirable to implement test delivery system 100 with a wide variety of computers 102 (or other hardware systems), stimulus output devices 106 and/or response input devices 110. Such computers 102 may be running a wide variety of software processes. Each such test delivery system 100 may exhibit different latencies. Accordingly, there is a desire to provide systems and methods for calibrating a stimulus-response test delivery system to account for such different latencies. Such calibration may permit stimulus-response results to be accurate, repeatable and/or comparable as between different testing systems.

SUMMARY

One aspect of the invention provides a method for calibrating a stimulus-response test system comprising a stimulus output device for delivering stimulus to a subject and a response input device for receiving a response from the subject. The method involves: sensing the stimulus output by the stimulus output device; recording a calibrator stimulus time associated with detection of a stimulus event; generating a calibrator response after detection of the stimulus event; recording a calibrator response time associated with generation of the calibrator response; and determining a latency value $t_{lat}$ associated with the stimulus-response test system based at least in part on a calibrator time difference $t_{stim/resp}$, the calibrator time difference $t_{stim/resp}$ comprising a difference between the calibrator response time and the calibrator stimulus time.

Another aspect of the invention provides a calibration system for calibrating a stimulus-response test system comprising a stimulus output device for delivering stimulus to a subject and a response input device for receiving a response from the subject. The calibration system comprises: a sensor for sensing the stimulus output by the stimulus output device; a calibration controller connected to receive a sensor signal from the sensor and configured to: detect a stimulus event based on the sensor signal; record a calibrator stimulus time associated with detection of the stimulus event; generate a calibrator response after detection of the stimulus event; and record a calibrator response time associated with generation of the calibrator response.

Another aspect of the invention provides a method for calibrating a stimulus-response test system comprising a stimulus output device for delivering stimulus to a subject and a response input device for receiving a response from the subject. The method comprises: sensing the stimulus output by the stimulus output device; recording a calibrator stimulus time associated with detection of a stimulus event; sensing the subject's response to the stimulus event; recording a calibrator response time associated with sensing the subject's response; and determining a latency value $t_{lat}$ associated with the stimulus-response test system based at least in part on a calibrator time difference $t_{stim/resp}$, the calibrator time difference $t_{stim/resp}$ comprising a difference between the calibrator response time and the calibrator stimulus time.

Another aspect of the invention provides a calibration system for calibrating a stimulus-response test system comprising a stimulus output device for delivering stimulus to a subject and a response input device for receiving a response from the subject. The calibration system comprises: a stimulus sensor for sensing the stimulus output by the stimulus output device; a response sensor for sensing the subject's response to a stimulus event; a calibration controller connected to receive a sensor signal from the stimulus sensor and configured to: detect a stimulus event based on the sensor signal; record a calibrator stimulus time associated with detection of the stimulus event; and record a calibrator response time associated with sensing the subject's response.

Further aspects and features of specific embodiments will become apparent by reference to the drawings and by study of the following detailed description and the accompanying drawings.

BRIEF DESCRIPTION OF THE DRAWINGS

In drawings which depict non-limiting embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Aspects of the invention provide systems and methods for calibrating a stimulus-response test system comprising a stimulus output device for delivering stimulus to a subject and a response input device for receiving a response from the subject. The calibration involves: sensing the stimulus output by the stimulus output device; recording a calibrator stimulus time associated with detection of a stimulus event; generating a calibrator response after detection of the stimulus event; recording a calibrator response time associated with generation of the calibrator response; and determining a latency value $t_{lat}$ associated with the stimulus-response test system based at least in part on a calibrator time difference $t_{stim/resp}$, the calibrator time difference $t_{stim/resp}$ comprising a difference between the calibrator response time and the calibrator stimulus time.

Figure 1:
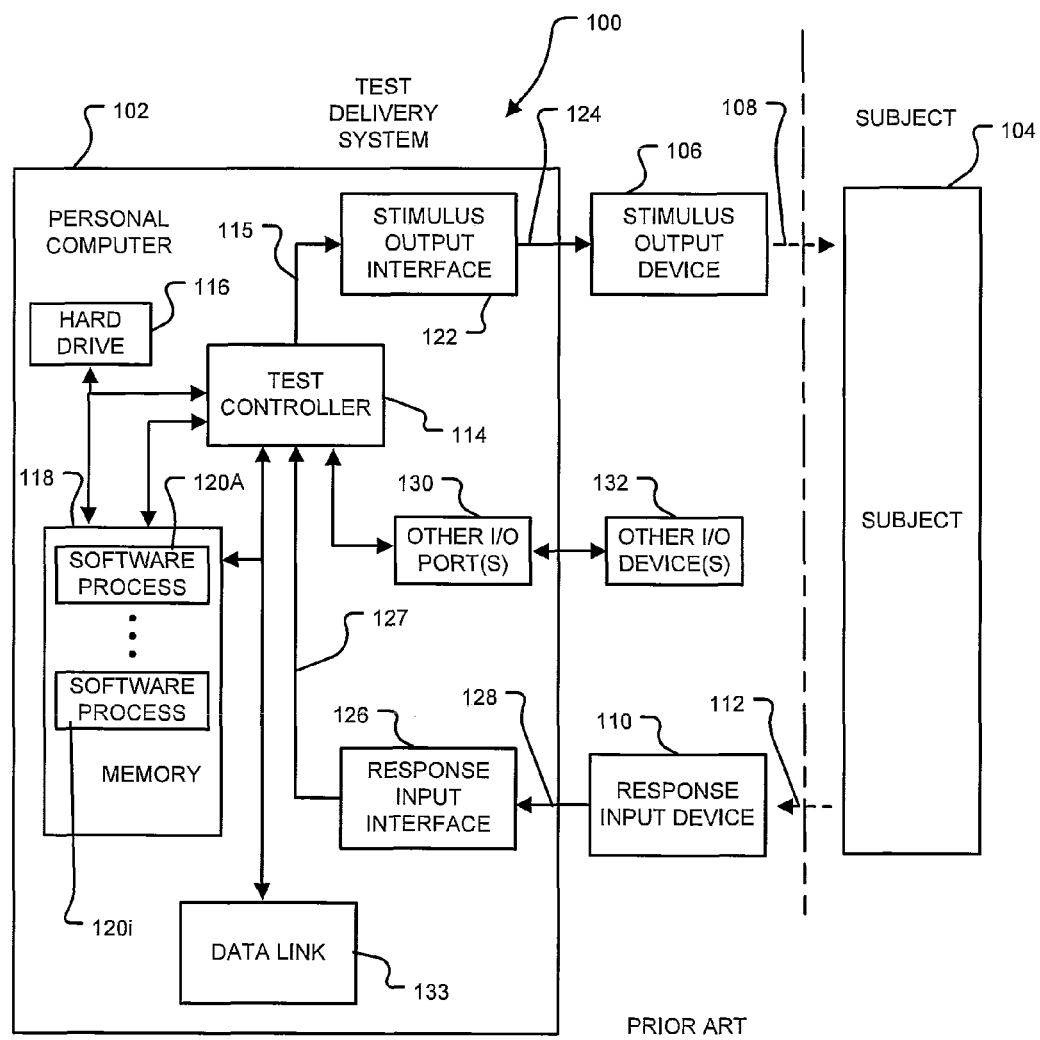
FIG. 1 is a schematic block diagram representation of a stimulus-response test delivery system.

The various embodiments of calibration systems and methods described herein may be generally used to calibrate neurobehavioural testing systems that measure and/or record one or more characteristics of a subject's (e.g. human or animal) responses to stimuli. Such testing systems may be referred to herein as "stimulus-response" test systems. In some embodiments, such systems may also generate the stimuli. By way of non-limiting example, the types of response characteristics which may be measured and/or recorded by stimulus-response test systems include the timing of a response (e.g. relative to the timing of a stimulus), the intensity of the a response, the accuracy of a response and/or the like. While there may be many variations of such stimulus-response test systems, for illustrative purposes, this description considers the FIG. 1 stimulus-response test system 100 and assumes that test system 100 is being used to administer a psychomotor vigilance task (PVT) test. As discussed above, controller 114 outputs a suitable signal 115 which causes stimulus output interface 122 to output signal 124 and stimulus output device 106 to output a corresponding stimulus 108. Stimulus 108 output by stimulus output device 106 may include a stimulus event (described in more detail below). When subject 104 perceives a stimulus event to be of the type for which a response is desired, subject 104 responds 112 using response input device 110. Response input device 110 generates a corresponding response signal 128 at response input interface 126 which is then directed to controller 114 as test-system response signal 127.

Test controller 114 may measure and/or record various properties of the stimulus-response sequence. Such properties may include estimates of the times at which a stimulus event occurred within stimulus 108 and a response 112 was received by test system 100. The time between these two events may be indicative of the time that it took subject 104 to respond to a particular stimulus event. In the absence of calibration information, the estimated times associated with these events may be based on the times at which controller 114 outputs signal 115 for stimulus output interface 122 and at which controller 114 receives test-system response signal 127 from response input interface 126. However, because of latencies associated with test system 100, the times at which controller 114 outputs signal 115 for stimulus output interface 122 and at which controller 114 receives test-system response signal 127 from response input interface 126 will not be the same as the times at which a stimulus event occurred within stimulus 108 and a response 112 was received by test system 100. More particularly, the time between controller 114 outputting signal 115 for stimulus output interface 122 and receiving test-system response signal 127 from response input interface 126 may be described as $t_{tot}$ where $t_{tot}=t_{stim/resp}+t_{lat}$ and $t_{stim/resp}$ represents the time of the actual response of subject 104 (i.e. the difference between the times at which a stimulus event occurred within stimulus 108 and a response 112 was received) and $t_{lat}$ is a latency parameter associated with test system 100. The latency parameter $t_{lat}$ may represent, for example, the latency between the recorded time of the output of signal 115 by controller 114 and the time that a stimulus event is actually output as a part of stimulus 108, the latency between the time that response 112 is generated by subject 104 and the time that test-system response signal 127 is recorded by controller 114 and/or other latencies.

Stimulus-response test system 100 may also include a data communications link 133. Such data communications link 133 may be a wired link (e.g. an ethernet link and/or modem) or a wireless link. Stimulus-response test system 100 may include other features and/or components not expressly shown in the FIG. 1 schematic drawing. By way of non-limiting examples, such features and/or components may include features and/or components common to personal computers, such as computer 102.

Figure 2A:
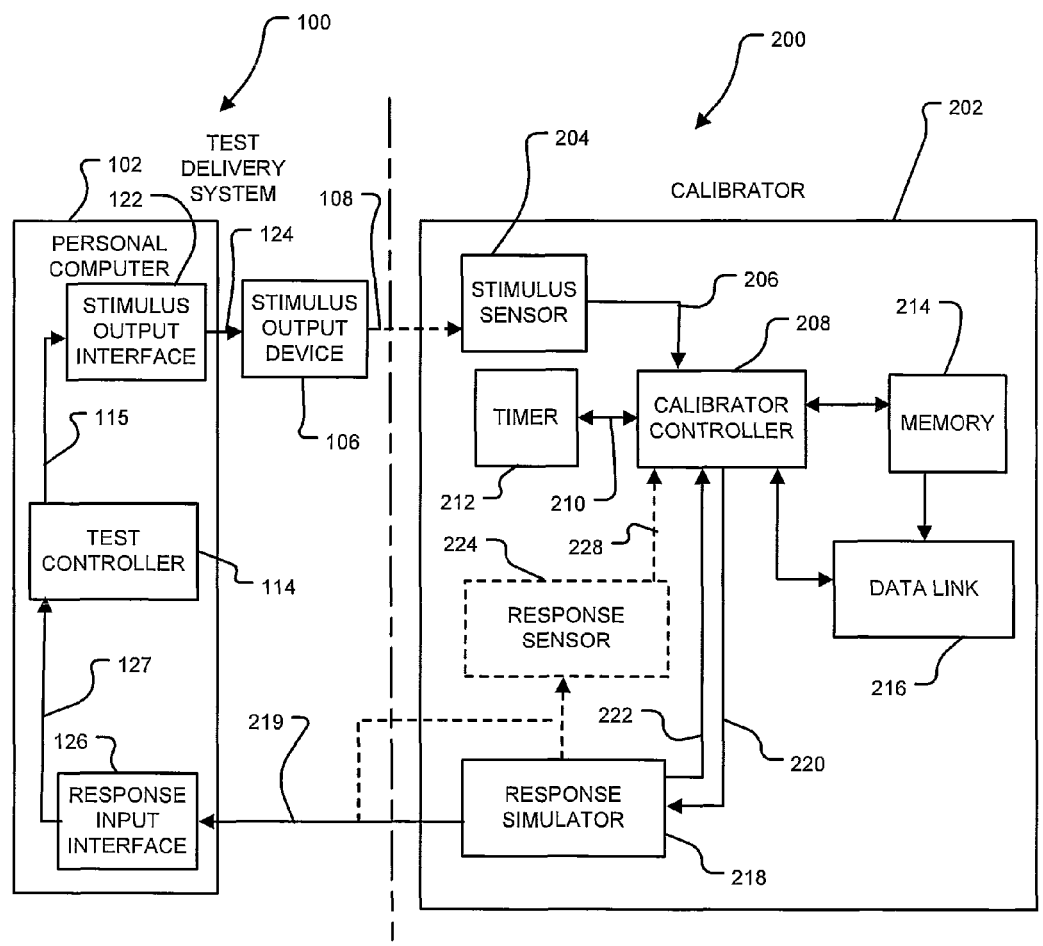
FIG. 2A is a schematic block diagram illustration of a calibrator system according to a particular embodiment being used to calibrate a stimulus-response test delivery system.
Figure 2B:
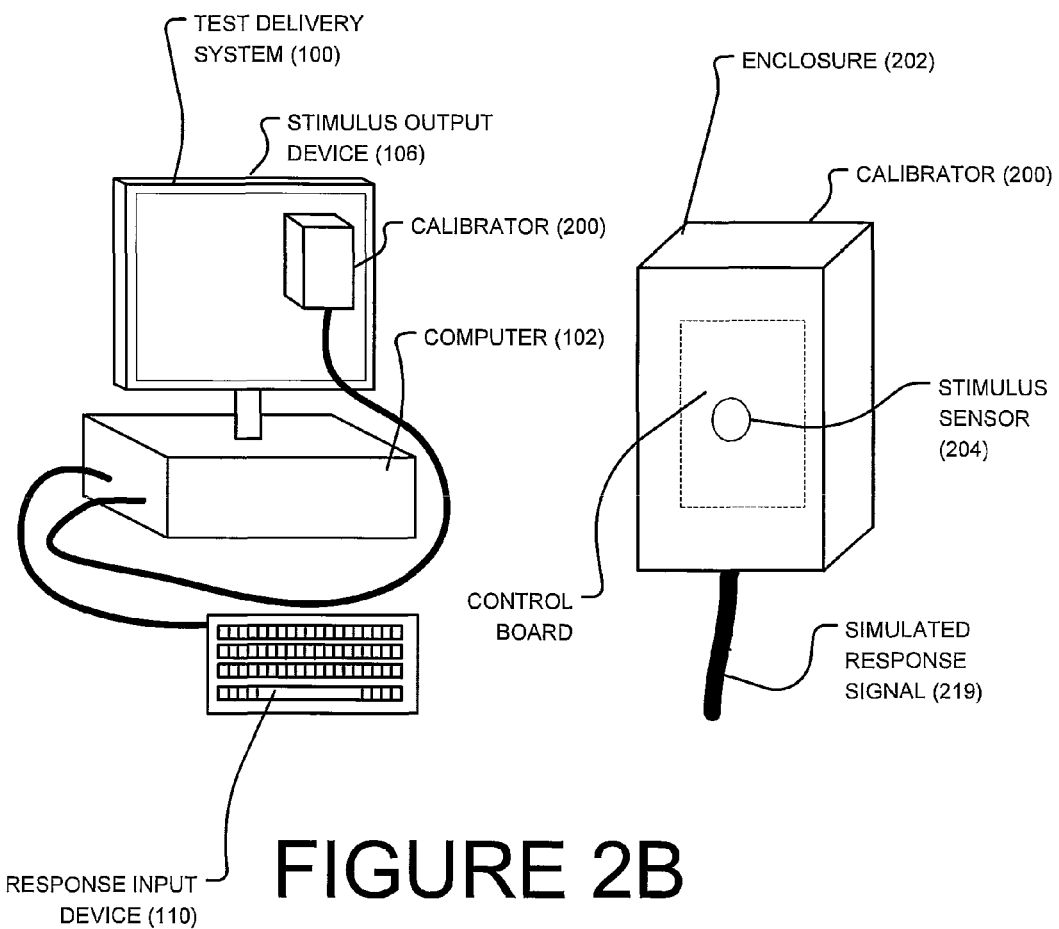
FIG. 2B is a pictoral illustration of a particular embodiment of the FIG. 2A calibrator system.

FIG. 2A is a block diagram representation of test system 100 and a calibration system 200 according to a particular embodiment. Portions of test system 100 are omitted from the FIG. 2A illustration for clarity. FIG. 2B is a pictoral view of test system 100 and calibration system 200 shown schematically in FIG. 2A. Calibration system 200 may be used to calibrate test system 100 by estimating a latency associated therewith. For example, calibration system 200 may be used to estimate the above-discussed parameter $t_{lat}$. Calibration system 200 may communicate such latency estimates back to test system 100 such that future stimulus-response test administered by test system 100 may provide calibrated stimulus-response timing information.

In the embodiment of FIGS. 2A and 2B (collectively, FIG. 2), calibration system 200 is housed within a housing 202 and comprises a stimulus sensor 204 that detects the occurrence of stimulus 108 output by stimulus output device 106. By way of non-limiting example, stimulus sensor 204 may comprise one or more of: a photosensitive sensor comprising one or more photodiodes or phototransistors, an audio sensor such as a microphone, or a 2-dimensional optical sensor such as a camera or video recorder and/or the like. In general, stimulus sensor 204 may be chosen to detect the characteristics of output 108 generated by stimulus output device 106. For example, where stimulus output device 106 comprises a light transmitting device that changes light intensity to provide stimulus 108, stimulus sensor may comprise one or more photodetectors.

In response to stimulus 108, stimulus sensor 204 outputs a signal 206 which is received by calibrator controller 208. While not expressly shown in the FIG. 2A illustration, calibrator 200 may comprise suitable signal conditioning hardware and/or software in the signal path between stimulus sensor 204 and calibrator controller 208. Such signal conditioning hardware and/or software is well known to those skilled in the art and may be used to condition signal 206 to make it suitable for receipt by calibrator controller 208. By way of non-limiting example, such signal conditioning hardware and/or software may include amplifiers, drivers, filters, A/D and/or D/A converters, buffers, logic circuitry and/or the like.

Calibrator controller 208 may comprise, for example, one or more suitably programmed data processors, together with suitable hardware, including, by way of non-limiting example: accessible memory, logic circuitry, drivers, amplifiers, A/D and D/A converters and like. Calibration controller 208 may comprise, without limitation, a microprocessor, a computer-on-a-chip, the CPU of a computer, any other suitable microcontroller and/or programmable logic circuitry. Controller 208 may comprise a plurality of data processors. In the illustrated embodiment of FIG. 2, calibration controller 208 is implemented by a suitably programmed microprocessor embedded in enclosure 202 of calibrator 200 and dedicated to the calibration operation of calibrator 200.

Calibration controller 208 monitors signal 206 and detects particular stimulus events based on signal 206. In general, stimulus events may comprise any event associated with stimulus 108 which may be observed by subject 104 (or for which it may be desired to test the ability of subject 104 to observe). By way of non-limiting example, stimulus events which may be detected by calibration controller 208 may include: the presence/absence of stimulus 108, the transition of a characteristic (e.g. intensity, frequency or the like) of stimulus 108 across a threshold, the presence or absence of a particular type of stimulus (e.g. shape of a visual object, tone of a auditory signal), a sequence of particular stimuli or the like. The types and characteristics of stimulus events detectable by calibration controller 208 based on signal 206 may be user-configurable. When calibration controller 208 determines that it has detected a particular stimulus event, calibration controller 208 records a time associated with the stimulus event. In the illustrated embodiment, calibration controller 208 receives a timing signal 210 from timer 212 and records a value associated with timing signal 210 when it detects a stimulus event. In other embodiments, calibration controller 208 may comprise an internal timing mechanism. Calibration controller 208 may optionally record the time associated with the stimulus event in memory 214. In some embodiments, calibration controller 208 may comprise sufficient internal memory to record the times associated with stimulus events.

After receiving a stimulus event, calibration controller 208 determines a desired response and sends a corresponding response signal 220 to response simulator 218. After detecting a stimulus event based on signal 206, calibration controller 208 may wait for a delay period before outputting response signal 220. Such a delay period, which may be random and/or user-configurable, may be similar to a range of delay periods associated with a typical response of subject 104. Such a delay period is not necessary, however, as calibration controller 208 may output response signal 220 immediately after detecting a stimulus event. While not expressly shown in the FIG. 2A illustration, calibrator 200 may comprise suitable signal conditioning hardware and/or software in the signal path between calibrator controller 208 and response simulator 218. Such signal conditioning hardware and/or software is well known to those skilled in the art and may be used to condition signal 220 to make it suitable for receipt and use by response simulator 218. By way of non-limiting example, such signal conditioning hardware and/or software may include amplifiers, drivers, filters, A/D and/or D/A converters, buffers, logic circuitry and/or the like.

In the FIG. 2 embodiment, response simulator 218 generates and outputs a simulated response signal 219 which is received by response input interface 126 of test system 100. Simulated response signal 219 generated by response simulator 218 is similar to the response signal 128 that test system 100 and response input interface 126 would expect from a subject 104 generating response signal 128 using response input device 110 (see FIG. 1). For example, where response input device 110 is a USB-based mouse or keyboard and response input interface 126 is a USB port, then response simulator 218 can generate a simulated response signal 219 that would be similar to the response signal 128 expected at USB response input interface 126 when subject 104 presses a mouse or keyboard button and response simulator 218 can deliver simulated response signal 219 directly to USB response input interface 126. As another example, where response input device 110 is a wireless (e.g. blue tooth) mouse and response input interface 126 is a wireless input port, response simulator 218 can generate a simulated response signal 219 similar to the response signal 128 expected at wireless input interface 126 when subject 104 presses a mouse button and response simulator 218 can deliver simulated response signal 219 directly to wireless response input interface 126.

Response simulator 218 may be implemented by a combination of software and hardware. In some embodiments, response simulator 218 may be implemented in whole or in part by calibration controller 208.

While not expressly shown in the FIG. 2A illustration, calibrator 200 may comprise suitable signal conditioning hardware and/or software in the signal path between response simulator 218 and response input interface 126. Such signal conditioning hardware and/or software is well known to those skilled in the art and may be used to condition simulated response signal 219 to make it suitable for receipt and use by response input interface 126. By way of non-limiting example, such signal conditioning hardware and/or software may include amplifiers, drivers, filters, A/D and/or D/A converters, buffers, logic circuitry and/or the like.

In the FIG. 2 embodiment, response simulator 218 of calibrator 200 outputs a return signal 222 when it has output simulated response signal 219. Return signal 222 is delivered to calibration controller 208 to indicate that simulated response signal 219 has been output. Upon receiving return signal 222, calibrator controller 208 records a time associated with simulated response 219. In the illustrated embodiment, calibration controller 208 receives a timing signal 210 from timer 212 and records a value associated with timing signal 210 when it receives return signal 222. In other embodiments, calibration controller 208 may comprise an internal timing mechanism. Calibration controller 208 may optionally record the time associated with the receipt of return signal 222 in memory 214. In some embodiments, calibration controller 208 may comprise sufficient internal memory to record the times associated with the receipt of return signals 222. In some embodiments, return signal 222 may include information about other characteristics of simulated response 219 which may be recorded by calibration controller 208. By way of non-limiting example, such characteristics may include the intensity of the response, the accuracy of the response and/or the like.

In addition to or in the alternative to return signal 222, calibrator 200 may comprise an optional response sensor 224 which detects simulated response 219 and outputs return signal 228 to calibration controller 208. Response sensor 224 may detect or sense simulated response 219 directly and/or from response simulator 218. Calibration controller 208 may handle the receipt of return signal 228 in a manner similar to that discussed above for return signal 222 to obtain a time associated with simulated response 219. In embodiments, where calibration controller 208 receives return signal 222 and return signal 228, calibration controller 208 may use the times 210 associated with one or the other of return signals 222, 228 as the time associated with simulated response 219, or may use an average of the times 210 associated with return signals 222, 228 as the time associated with simulated response 219. Response sensor 224 may sense additional characteristics of simulated response signal 219 (i.e. in addition to the timing of simulated response signal 219) and may provide such characteristics to calibration controller 208 as part of return signal 228. Non-limiting examples of other response characteristics include: intensity of the response, mechanical force of the response, speed of mechanical motion of associated with the response, or accuracy of the response (e.g. response location in a cases where test system 100 expects a response that includes a spatial target). Such additional response characteristics may also be recorded by calibration controller 208 (e.g. in memory 214).

Information (including timing information and any additional response characteristics) measured and/or recorded by calibrator 200 may be transmitted (e.g. from calibration controller 208 and/or from memory 214) to external systems using data link 216. External systems to which such information may be transmitted may include, for example, stimulus-response test system 100. The data may be transmitted intermittently (e.g. after each stimulus event and/or response event) or as a batch (e.g. at the conclusion of one or more test sequences).

FIG. 2B shows an example of a physical embodiment of test system 100 and calibration system 200 depicted in FIG. 2A. In the FIG. 2B embodiment, test system 100 comprises a personal computer 102, that uses a keyboard as response input device 110 and a monitor/display as stimulus output device 106. By way of non-limiting example, test system 100 may administer a psychomotor vigilance task (PVT) test. The PVT test outputs stimuli that may include the appearance of a symbol on stimulus output device (monitor) 106, or the appearance of numeric values that update on the screen based on elapsed time since the start of the stimulus (e.g. a millisecond stop-watch display). Subject 104 is expected to press a key on response input device (keyboard) 110 in the shortest possible time after observing a stimulus event. Response input device (keyboard) 110 may be plugged into a USB response input interface 126 (not specifically enumerated in FIG. 2B). After each response, a new stimulus event may be shown with a random inter-stimulus event interval, until the test concludes. The test may conclude based on a total elapsed time since the start of the test (e.g. 5 minutes) or some other test-end criteria (e.g. a user-configurable or constant number of stimulus-response events and/or the like).

Calibrator 200 of the FIG. 2B exemplary embodiment comprises an enclosure 202 that houses a stimulus sensor 204 (e.g. a photodetector) and a control board (not specifically enumerated). In the FIG. 2B embodiment, the control board includes some of the electronics associated with calibrator 200 including, for example, calibration controller 208, timer 212, memory 214, response simulator 218 and response sensor 224. In other embodiments, any of these components may be implemented on separate boards and/or in separate enclosures. When a calibration is being conducted in the FIG. 2B embodiment, response input device (keyboard) 110 is unplugged from response input interface (USB port) 126 and response simulator 218 is plugged into response input interface 126 such that simulated response signal 219 can be delivered to response input interface 126. In some embodiments, response input keyboard 110 may remain plugged in and response simulator 218 may be plugged into a different response input USB interface 126, but this may not be as desirable as different USB ports may experience different latencies.

In operation, test system controller 114 may operate in a calibration mode which may involve transmitting one or more stimulus events to calibrator 200 via stimulus output interface 122 and stimulus output device 106 and then receiving corresponding simulated responses via response input interface 126. For each of the one or more stimulus events, test controller 114 can measure and/or record the time difference $t_{tot}$ between controller 114 outputting signal 115 for stimulus output interface 122 and receiving test-system response signal 127 from response input interface 126. In addition, for each of the one or more stimulus events, calibrator 200 can measure and/or record the time difference between receiving the stimulus event at stimulus sensor 204 (e.g. via signal 206) and outputting a simulated response (e.g. via one or both of return signals 222, 228). This time difference represents a simulated value of the stimulus-response time of subject 104 $t_{stim/resp}$. The difference between the time difference values recorded by test controller 114 $t_{tot}$ and the time difference values recorded by calibrator 200 $t_{stim/resp}$ represents an estimate of the latency $t_{lat}$ of test delivery system 100.

following the conclusion of a calibration operation, calibrator 200 may transmit its recorded time difference values $t_{stim/resp}$ test controller 114 and/or to some other external system via data link 216. In other embodiments, calibrator 200 may transmit its recorded time difference values $t_{stim/resp}$ to test controller 114 and/or to some other external system at intermittent times during a test, such as after each stimulus event/response sequence or at some other suitable interval. After receiving the time difference values $t_{stim/resp}$, test controller 114 (and/or the other external system) may use the time difference values $t_{stim/resp}$ to obtain latency estimates $t_{lat}$ by performing difference calculations as discussed above (e.g. $t_{lat}=t_{tot}-t_{stim/resp}$). Latency estimates $t_{lat}$ may also be referred to as calibration values $t_{lat}$. In some embodiments, test controller 114 (and/or the other external system) may perform statistical analysis on the latency estimates $t_{lat}$ to obtain an expected latency value $E[t_{lat}]$ (where $E[\cdot]$ represents the expected value operator) and/or the deviation/variance of the latency estimates. Mathematical and computational techniques for determining such statistical information from a measured sample set are well known.

Once the expected value and variance of the latency $t_{lat}$ of test system 100 have been estimated, calibrator 200 can be removed from test system 100 and, to the extent it was removed, response input device (e.g. keyboard) 110 can be plugged back into response input interface (e.g. USB port) 126. Thereafter, stimulus-response test results obtained by test system 100 on a subject 104 (e.g. the $t_{tot}$ values representing the difference between the time that test controller 114 outputs signal 115 to stimulus output interface 122 and the time that test controller 114 receives test-system response signal 127 from response input interface 126) may be offset by the expected latency $E[t_{lat}]$ to obtain more accurate results of the stimulus-response time $t_{stim/resp}$ of subject 104 according to $t_{stim/resp}=t_{tot}-E[t_{lat}]$. Similarly, a confidence or variance of the stimulus-response time $t_{stim/resp}$ of user 104 may be determined using the variance of the latency values. In other embodiments, statistical analysis is not required or used and the stimulus-response time $t_{stim/resp}$ of subject 104 may be determined according to $t_{stim/resp}=t_{tot}-t_{lat}$ where $t_{lat}$ represents an individual latency estimate.

Figure 3A:
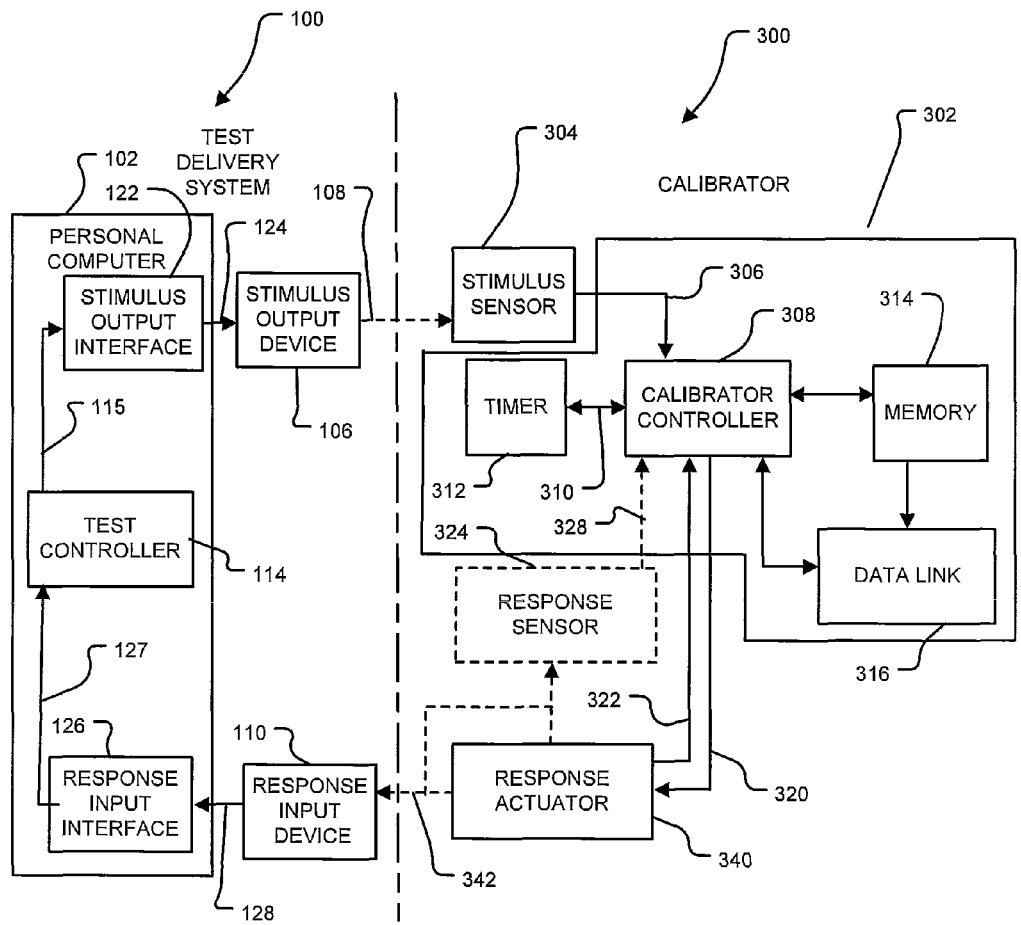
FIG. 3A is a block diagram illustration of a calibrator system according to an example embodiment being used to calibrate a stimulus-response test delivery system.
Figure 3B:
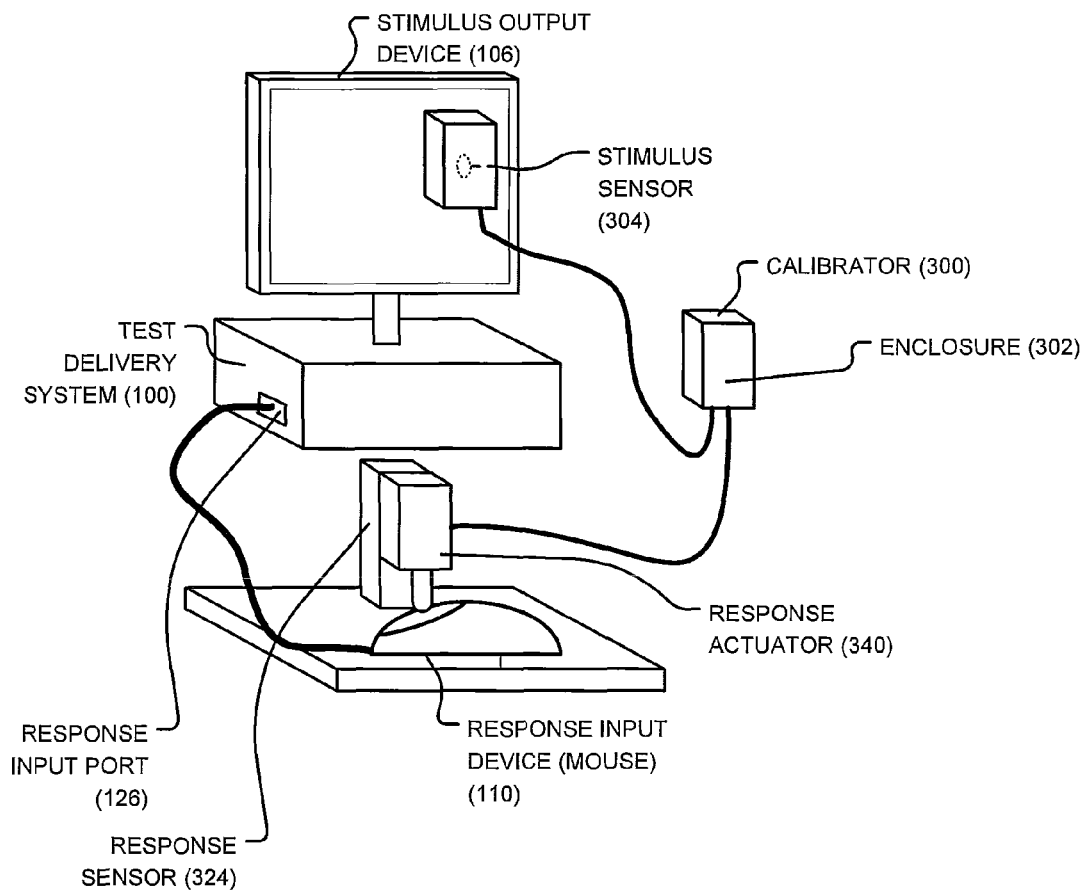
FIG. 3B is a pictoral illustration of a particular embodiment of the FIG. 3A calibrator system.

FIGS. 3A and 3B (collectively, FIG. 3) schematically illustrate stimulus-response test system 100 with a calibration system 300 according to another embodiment. Calibration system 300 is similar in many respects to calibration system 200 described above. Features and components of calibration system 300 that are similar to corresponding features and components of calibration system 200 are designated with similar reference numerals, except that the features and components of calibration system 300 are preceded by the numeral '3' and similar features and components of calibration system 200 are preceded by the numeral '2'. Calibration system 300 differs from calibration system 200 primarily in that calibration system 300 includes a response actuator 340 which actuates response input device 110 of test system 100. Response actuator 340 of calibrator 300 may replace response simulator 218 of calibrator 200. Response actuator 340 may permit calibration of test system 100 without removing response input device 110 and may actually incorporate latencies associated with response input device 110 and response signal 128 into the calibration. In the FIG. 3A illustration, the actuation of response input device 110 by response actuator 340 is enumerated 342.

Response actuator 340 may be responsive to a response signal 320 from calibration controller 308. Response signal 320 may be generated in a manner similar to the generation of response signal 220 described above for calibrator 200. For example, calibration controller 308 may generate response signal 320 in response to detection of a stimulus event based on signal 306 received from stimulus sensor 304 which in turn is based on stimulus 108 generated by stimulus output device 106. While not expressly shown in the FIG. 3A illustration, calibrator 300 may comprise suitable signal conditioning hardware and/or software in the signal path between calibration controller 308 and response actuator 340. Such signal conditioning hardware and/or software is well known to those skilled in the art and may be used to condition response signal 320 to make it suitable for receipt and use by response actuator 340 (e.g. to drive response actuator 340). By way of non-limiting example, such signal conditioning hardware and/or software may include amplifiers, drivers, filters, A/D and/or D/A converters, buffers, logic circuitry and/or the like.

In general, response actuator 340 provide actuation 342 of response input device 110 in response to signal 320 from calibration controller 308. Non-limiting examples of a response actuator 340 include: a mechanical actuator (e.g. a solenoid, electrical motor and/or the like) that moves in response to signal 320 to provide actuation 342 of response input device 110, a light/radiation generator (e.g. a light emitting diode, incandescent bulb, laser generator and/or the like) that generates electromagnetic radiation in response to signal 320 to provide actuation 342 of response input device 110, an acoustic generator (e.g. a speaker, a vibrational device and/or the like) that generates an acoustic signal in response to signal 320 to provide actuation of response input device 110 and/or the like. The particular type of response actuator 340 incorporated into calibration system 300 may be selected to match the particular type of response input device 110 used in stimulus-response test system 100. For example, if response input device 110 comprises a mouse with a button depression as the actuation event (as is the case, for example, in the illustrated embodiment of FIG. 3B), then response actuator 340 may comprise a solenoid-based actuator with sufficient force and movement range to depress the mouse button of response input device 110. Such a solenoid-based response actuator 340 and/or response input device 110 may be mounted on a suitable jig which permits response actuator 340 and response input device to be securely positioned with respect to one another.

Response actuator 340 may comprise a control system incorporating feedback (not expressly shown) which may be used to control the characteristics of the actuation 342 of response input device 110. For example, such control systems and feedback may be used to cause response actuator 340 to track a reference characteristic (e.g. a reference response actuation level). Feedback used in such control systems may comprise one or more feedback sensors. By way of non-limiting example, such feedback sensors could comprise one or more force feedback sensors (e.g. a current sensor on a solenoid), position feedback sensors (e.g. a linear encoder on a solenoid), optical feedback sensors, acoustic feedback sensors (e.g. a microphone) and/or the like.

Like calibrator 200, calibrator 300 may include an optional response sensor 324. However, in contrast to sensing a simulated response signal 219, optional response sensor 324 of calibrator 300 may sense actuation 342 directly and/or from response actuator 340. While not shown in FIG. 3A, optional response sensor 324 of calibrator 300 may additionally or alternatively sense response signal 128 either directly or from response input device 110. In the illustrated embodiment of FIG. 3B, response sensor 324 comprises a linear encoder. In other embodiments, response sensor 324 may comprise other types of sensor which may depend on the type of response actuator 340 and/or actuation 342. By way of non-limiting example, response sensor 324 may comprise: a position sensor (e.g. a linear encoder to detect position of a solenoid actuator 340), a pressure sensor to detect a pressure applied by response actuator 340, a microphone (to detect signals from an auditory response actuator 340), a electrical signal detection circuit (to detect transmission of electrical signal between response actuator 340 and response input device 110) an/or the like.

In the illustrated embodiment of FIG. 3, calibrator 300 also differs from calibrator 200 in that stimulus sensor 304, response actuator 340 and response sensor 324 are located externally to enclosure 302. This is not necessary. Any of these components may be housed (at least in part) within enclosure 302 or any of the components shown to be housed in enclosure 302 may be located externally to enclosure 302 and/or in different housings.

Figure 4A:
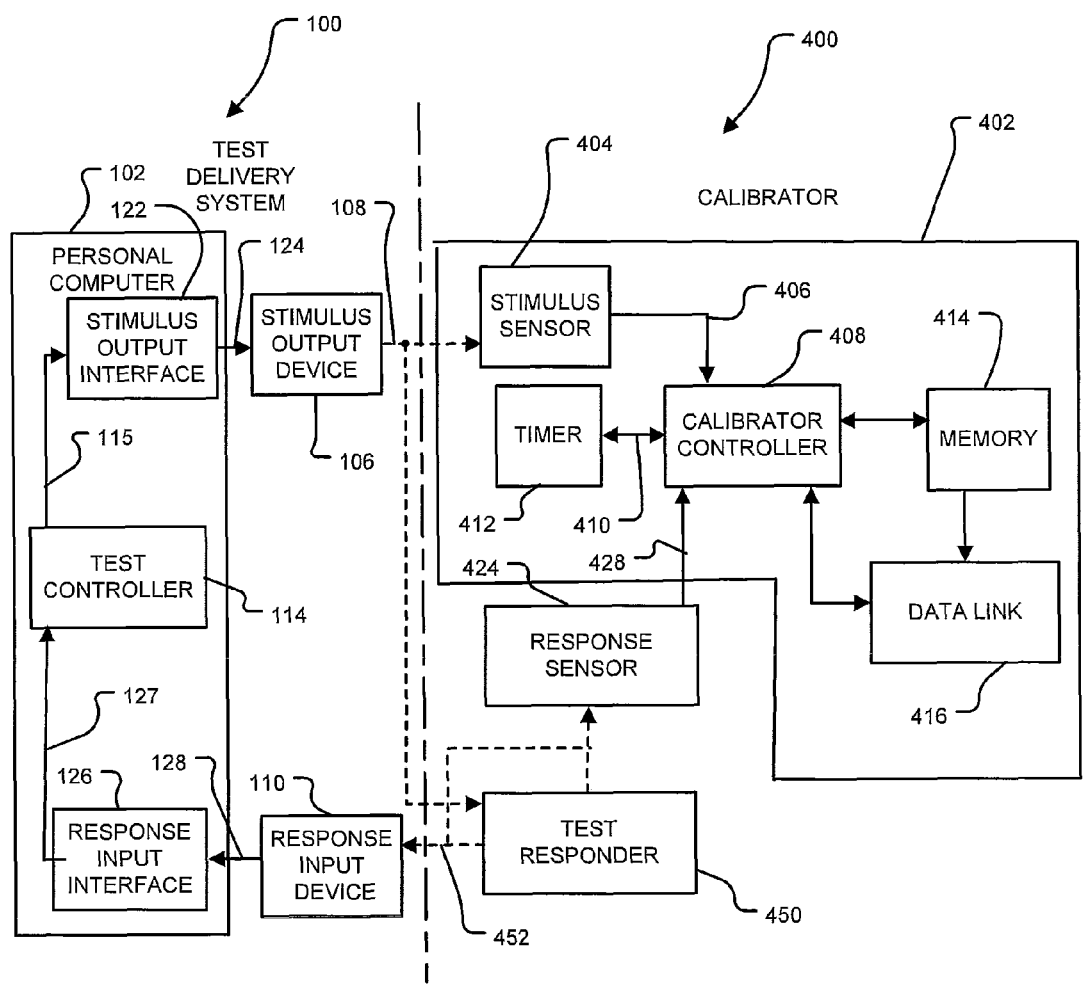
FIG. 4A is a block diagram illustration of a calibrator system according to another example embodiment being used to calibrate a stimulus-response test delivery system.
Figure 4B:
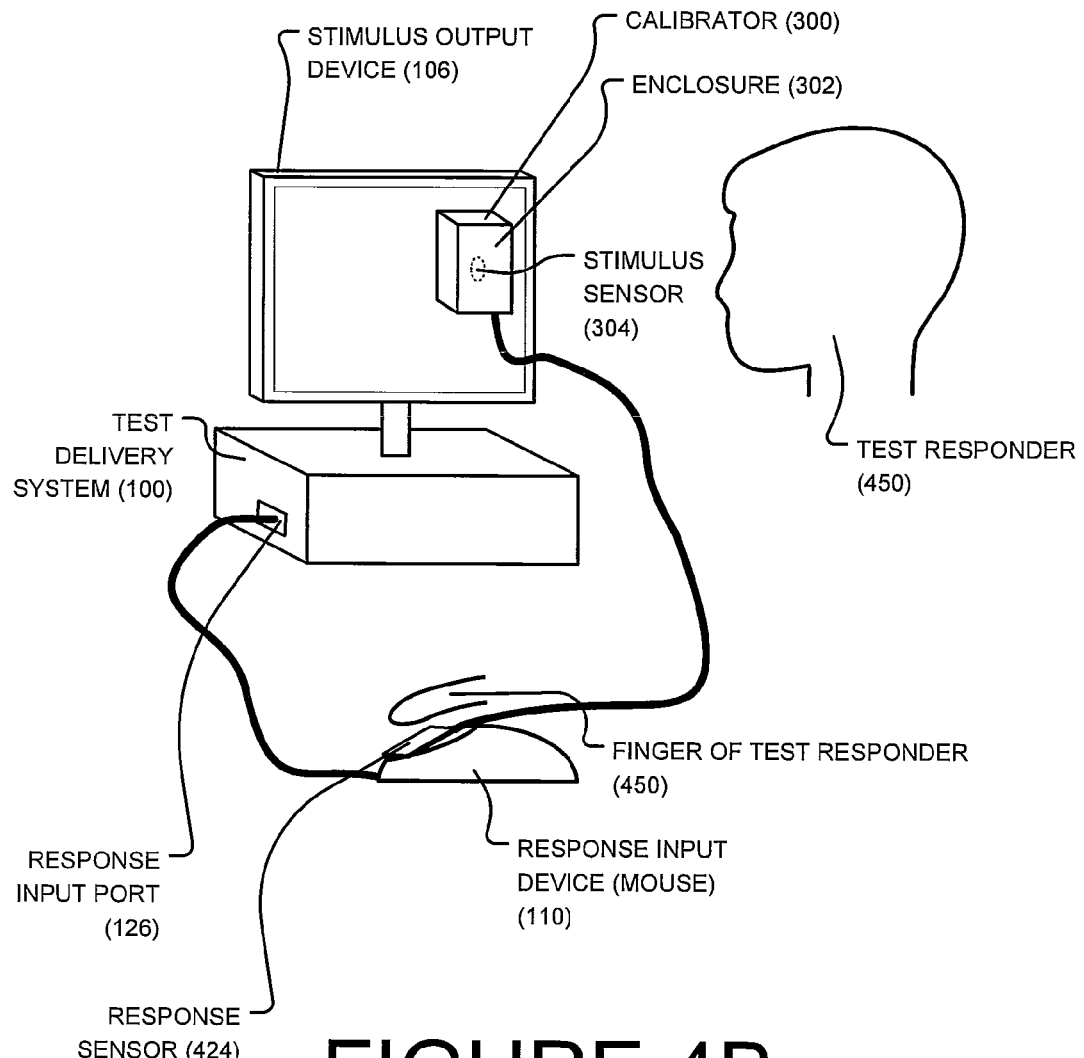
FIG. 4B is a pictoral illustration of a particular embodiment of the FIG. 4A calibrator system.

FIGS. 4A and 4B (collectively, FIG. 4) schematically illustrate stimulus-response test system 100 with a calibration system 400 according to another embodiment. Calibration system 400 is similar in many respects to calibration systems 200 and 300 described above. Features and components of calibration system 400 that are similar to corresponding features and components of calibration systems 200, 300 are designated with similar reference numerals, except that the features and components of calibration system 400 are preceded by the numeral '3' and similar features and components of calibration systems 200, 300 are preceded by the numeral '2' or '3' respectively. Calibration system 400 differs from calibration systems 200, 300 primarily in that calibration system 400 provides stimulus 108 to a test responder (e.g. a test subject or automated test responder) 450 and who responds directly (response 452) via response input device 110 of test system 100. Test responder 450 may replace response simulator 218 of calibrator 200 and/or response actuator 340 of calibrator 300. Further, calibration controller 408 does not use a response signal 220, 320, since test responder 450 does not have to be directed to output response 452. Like calibrator 300, calibrator 400 permits calibration of test system 100 without removing response input device 110 and may actually incorporate latencies associated with response input device 110 and response signal 128 into the calibration. Calibrator 400 may also permit measurement of the particular latency of a particular stimulus-response event, so that stimulus-response events can be calibrated on an individual basis.

calibrator 400 includes a response sensor 424 which senses response 452 of test responder 450 directly from response 452 and/or from test responder 450. While not shown in FIG. 4A, response sensor 424 of calibrator 400 may additionally or alternatively sense response signal 128 either directly or from response input device 110. In the particular embodiment of FIG. 4B, response sensor 424 may comprises a pressure sensor located to detect the pressure associated with the finger of test responder 450 on response input device (e.g. mouse) 110. In other embodiments, response sensor 424 may comprise other types of sensor which will depend on the type of response 452 expected of test responder 450. By way of non-limiting example, response sensor 424 may comprise any of the response sensors discussed above in connection with response sensor 324.

In the illustrated embodiment of FIG. 4, calibrator 400 is similar to calibrator 200 in that stimulus sensor 404 is located within enclosure 402. However, in the illustrated embodiment of FIG. 4, response sensor 424 is located externally to enclosure 402. This is not necessary. Response sensor 424 may be housed (at least in part) within enclosure 402 or any of the components shown to be housed in enclosure 402 may be located externally to enclosure 402 and/or in different housings.

Figure 5A:
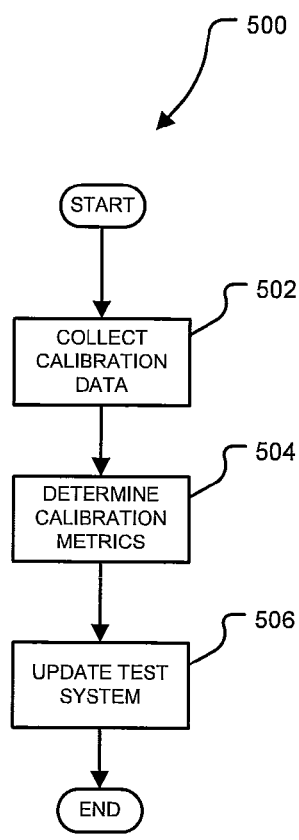
FIG. 5A is a flow chart of a method for generating calibration data, calculating calibration metrics, and updating the stimulation-response test system according to a particular embodiment.

FIG. 5A is a flow chart of a method 500 for calibrating stimulus-response tests according to a particular embodiment. Method 500 comprises collecting calibration data in block 502, determining calibration metrics in block 504 and updating the stimulus-response test system (e.g. test system 100) in block 506.

Figure 6:
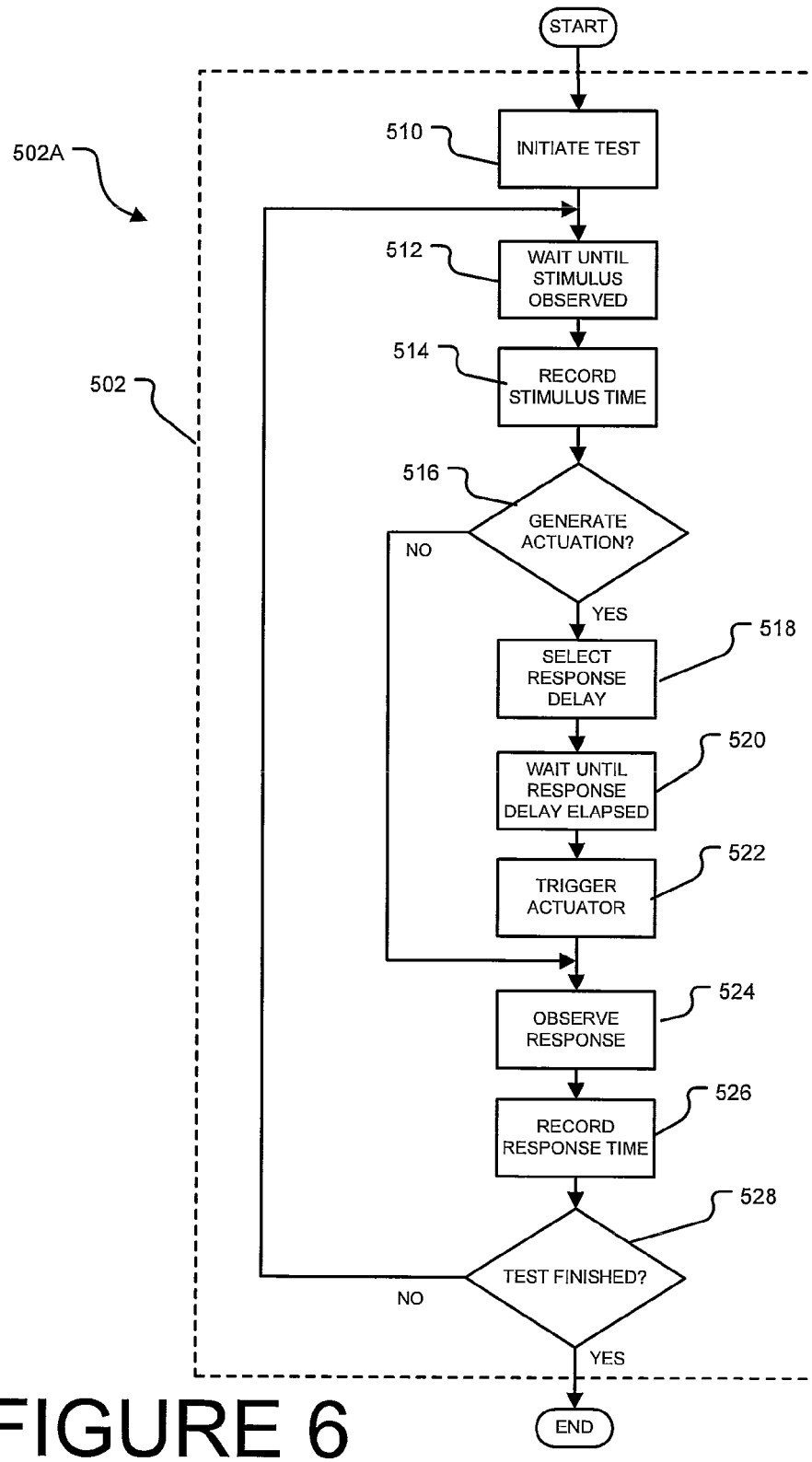
FIG. 6 is a flow chart of a method for generating calibration data which may be used as a part of the methods shown in FIGS. 5A and 5B in accordance with a particular embodiment.

FIG. 6 is a flow chart of a method 502A for implementing the block 502 procedure for collecting calibration data (FIG. 5A) according to a particular embodiment. Method 502A may be performed by the combination of test system and a corresponding calibrator. For the purposes of explaining method 502A, it will be assumed that the calibrator and test system are calibrator 200 and test system 100 described in FIG. 2A above. It will be appreciated however that method 502A may be generalized for any of the calibrator embodiments described herein.

Method 502A commences in block 510 which involves initiating a calibration operation. Initiating the calibration may involve manual action of a human operator and/or an automated action (e.g. a control signal) which may be generated by calibrator 200 and/or by test system 100. For example, calibrator 200 may determine that it is desirable to perform a calibration operation at periodic intervals and/or on the occurrence of a particular event (e.g. connection to a new test system 100). Once a calibration operation has begun, method 502A enters a loop which involves generating stimulus-response events and recording response times (e.g. the above discussed $t_{tot}$ and $t_{stim/resp}$) until it is determined in block 528 that the calibration operation is completed.

The method 502A loop begins in block 512 which involves generating a stimulus event. A bock 512 stimulus event may be generated by test controller 114 as described above. Block 512 may involve waiting a sufficiently long period to ensure that any processing associated with the previous iteration of the method 502A loop has completed. Method 52A then proceeds to block 514 which involves recording the times associated with stimulus events. The block 514 stimulus event time recordal may take place in both test system 100 and calibrator 200. As discussed above, test controller 114 may record the time associated with the output of signal 115 corresponding to a stimulus event and calibrator controller 208 may record the time associated with the detection of a stimulus event based on signal 206 from stimulus sensor 204. In some embodiments, where a stimulus event comprises the presence or absence of a stimulus 108, calibration controller 208 may poll stimulus sensor 204 at suitable intervals (e.g. every 0.5 ms).

Method 502A then proceeds to block 516 which involves an inquiry into whether calibrator 100 should generate a response corresponding to the stimulus event. The block 516 inquiry may be performed by calibration controller 208. In the case of calibrator 100 and calibrator 200 described above, the block 516 inquiry will be positive provided that the block 512 stimulus event is valid. However, in the case of calibrator 300, calibration controller 208 does not generate a response. Instead a response is generated by test responder 450. Consequently, in the case of calibrator 300, the block 516 inquiry will be negative and method 502A will jump down to block 524.

Assuming that the block 516 inquiry is positive, method 502A proceeds to a response sequence 517. Response sequence 517 may be performed by calibrator 200 (e.g. by calibration controller 208). Response sequence 517 involves selecting a response delay (block 518), waiting for the response delay to elapse (block 520) and then triggering a response (block 522). Non-limiting examples of methods for selecting the response delay in block 518 include: waiting for a constant (possibly user-configurable) delay (e.g. 300 ms), selecting a random delay from a probability distribution having an upper and lower bound (e.g. between 0 ms and 30 s), selecting delays sequentially increasing until an upper bound (e.g. a ramp function starting at 300 ms and increasing by 1 ms each iteration of the method 502A loop and resetting the delay to 300 ms once the delay has reached a threshold (e.g. 500 ms)). The block 318 wait may have a response time that is less than or equal to a desired accuracy of calibration. In the case of calibrator 200, triggering of a response in block 522 may involve outputting response signal 220 to response simulator 218. Similarly, in the case of calibrator 300, triggering of a response in block 522 may involve outputting a response signal 320 to response actuator 340.

Method 502A then proceeds to block 524 which involves observing a response and block 526 which involves recording the response times. The block 526 response time recordal may take place in both test system 100 and calibrator 200. As discussed above, test controller 114 may record the time associated with the receipt of test-system response signal 127 from response input interface 126 and calibrator controller 208 may record the time associated with the detection of a response event via return signal 222 from response simulator 224 and/or return signal 228 from response sensor 224. In the case of calibrator 300, the block 526 response recordal may involve the time associated with the receipt (by calibrator controller 308) of return signal 322 from response actuator 340 and/or return signal 328 from response sensor 324. In the case of calibrator 400, the block 526 response recordal may involve the time associated with the receipt (by calibrator controller 408) of return signal 428 from response sensor 424. In embodiments where the response time is determined from a response sensor (e.g. response sensor 224 of calibrator 200), block 524 may involve polling the response sensor at suitable time intervals (e.g. 0.5 ms). In calibrators where the response is initiated by a calibrator controller (e.g. calibrator controllers 208, 308 of calibrators 200, 200), the block 524 observation of a response may additionally or alternatively be accomplished by software being run on the calibration controller. For example, where the calibration controller executes software that causes it to output a response signal, then the calibration controller itself can observe that a response has occurred and can cause a time to be recorded in an instruction following the instruction which causes the response signal to be output.

At the conclusion of block 326, test system 100 has recorded a stimulus time and a response time (in blocks 514, 526). The difference between these two times recorded by test system 100 may be the total time $t_{tot}$ described above. Similarly, at the conclusion of block 526, calibrator 200 has recorded a stimulus time and a response time (in blocks 514, 526). The difference between these two times recorded by calibrator 200 may be the time $t_{stim/resp}$ described above.

After block 526, method 502A proceeds to block 528 which involves an inquiry into whether the method 502A calibration operation has concluded or not. If the block 528 inquiry is negative, then method 502A loops back to block 512 for another iteration (i.e. another stimulus-response sequence). If the block 528 inquiry is positive, then method 502A ends. It should be noted that method 502A may optionally include loop exit inquiries at multiple points (not explicitly shown in the FIG. 6 flow chart). Such an exit could be triggered by an external cancel command or the like.

Figure 7:
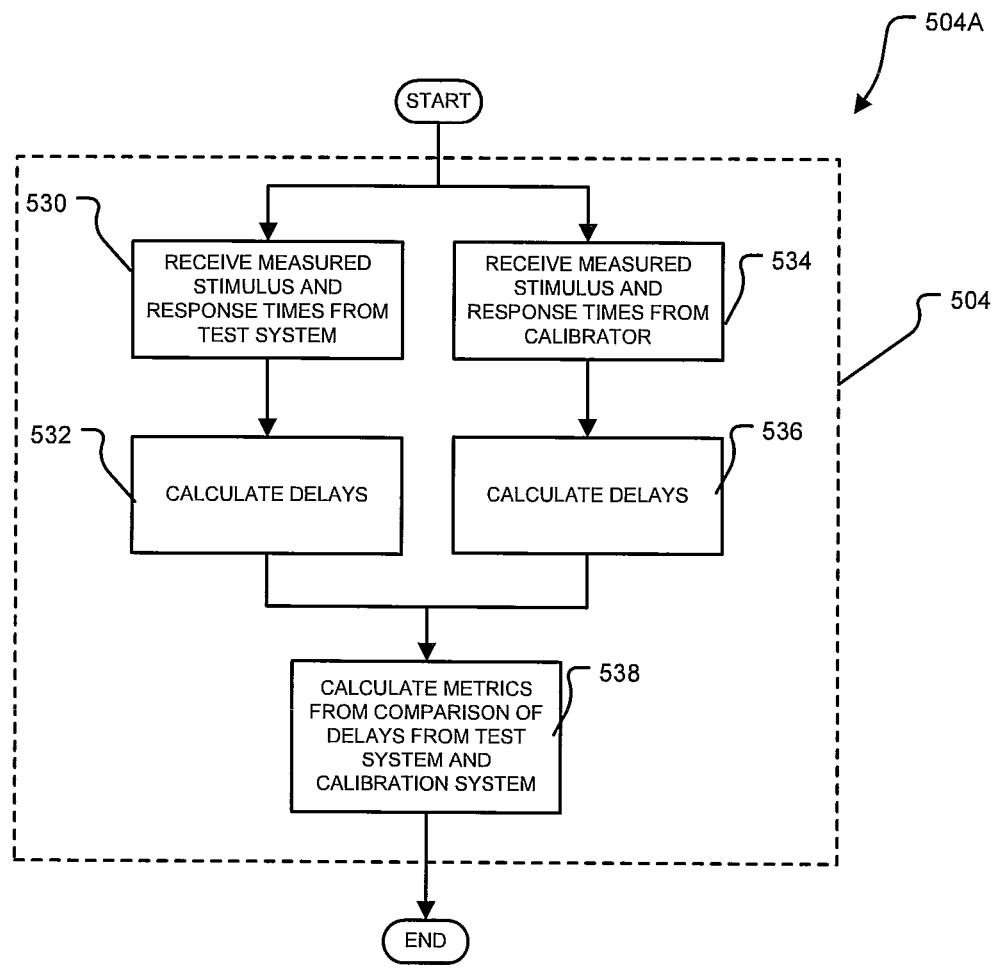
FIG. 7 is a flow chart of a method for calculating calibration metrics which may be used as a part of the methods shown in FIGS. 5A and 5B in accordance with a particular embodiment.

FIG. 7 is a flow chart of a method 504A for implementing the block 504 procedure for determining calibration metrics (FIG. 5A) according to a particular embodiment. Method 504A may be performed by the combination of test system and a corresponding calibrator. For the purposes of explaining method 504A, it will be assumed that the calibrator and test system are calibrator 200 and test system 100 described in FIG. 2A above. It will be appreciated however that method 504A may be generalized for any of the calibrator embodiments described herein.

Block 530 may involve receiving the measured stimulus and response times from test system 100. Such measured test system stimulus and response times from may come from blocks 514, 526 of method 502A as described above. In block 532, test controller 114 may calculate the test system delay $t_{tot}$ by finding a difference between the block 530 stimulus and response times. Block 534 may involve receiving the measured stimulus and response times from calibrator 200. Such measured calibrator stimulus and response times from may come from blocks 514, 526 of method 502A as described above. In block 536, calibrator controller 208 may calculate the calibrator delay $t_{stim/resp}$ by finding a difference between the block 534 stimulus and response times. The block 536 information may then be transmitted back to test controller 114 or to some other external system which may calculate latency metrics associated with test system 100 in block 538. In other embodiments, the block 532 test-system information may be transmitted to calibrator controller 208 which may calculate the test system delay $t_{tot}$ and/or other latency metrics associated with test system 100 in block 538. Such block 538 latency metrics may use the time difference values $t_{stim/resp}$ to obtain latency estimates $t_{lat}$ by performing difference calculations as discussed above (e.g. $t_{lat}=t_{tot}-t_{stim/resp}$). Latency estimates $t_{lat}$ may also be referred to as calibration values $t_{lat}$. In some embodiments, test controller 114 (and/or some external system) may perform statistical analysis on the latency estimates $t_{lat}$ to obtain an expected latency value $E[t_{lat}]$ (where $E[\cdot]$ represents the expected value operator) and/or the deviation/variance of the latency estimates. Mathematical and computational techniques for determining such statistical information from a measured sample set are well known.

Returning to FIG. 5A, updating the test system in block 506 may involve passing the block 504 calibration metrics to test system 100 (if they are not already known to test controller 114) so that test system 100 may correct test results when test system 100 is used to administer a stimulus-response test to a subject. For example, if test system 100 conducts a stimulus-response test on a subject 104 and determines that the total time $t_{tot}$, then the expected latency value $E[t_{lat}]$ determined in block 538 (FIG. 7) may be subtracted from the total time $t_{tot}$ to obtain an estimate of the subject's actual stimulus-response time $t_{stim/resp}$. Test system 100 may output the calibrated stimulus-response time $t_{stim/resp}$. Additionally or alternatively, test system 100 may output any suitable combination of the total time $t_{tot}$, the calibration value $E[t_{lat}]$ and the calibrated stimulus-response time $t_{stim/resp}$.

Figure 5B:
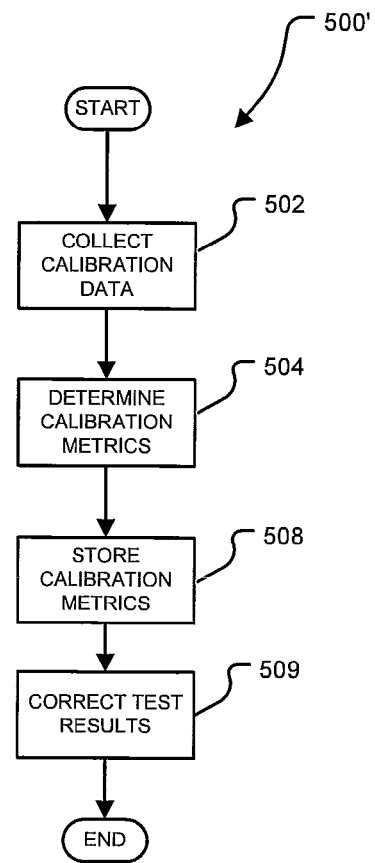
FIG. 5B is a flow chart of a method for generating calibration data, calculating calibration metrics, and correcting test results according to a particular embodiment.

FIG. 5B is a flow chart of a method 500' for generating calibration data (block 502), determining calibration metrics (block 504), and correcting test results (blocks 508, 509) according to a particular embodiment. Blocks 502, 504 are substantially similar to blocks 502, 504 described above. Block 508 involves recording or storing the block 504 calibration metrics. Block 509 involves using the stored calibration metrics to correct stimulus-response test results. Correcting test results may be performed by retrieving saved test results from previously conducted stimulus-response tests and adjusting reaction time data based on the saved calibration metrics prior to analyzing the data.

The systems and methods disclosed herein may be used to allow standardized comparison between stimulus-response tests taken on stimulus-response test systems with inter-test system variability due to differences in hardware or software. The systems and methods disclosed may also be used to correct for intra-test system variability due to drift or temporal variability on a given test system. The calibration systems and methods provide an objective and repeatable means to adjust reaction time data to match a common reference.

As will be apparent to those skilled in the art in the light of the foregoing disclosure, many alterations and modifications are possible in the practice of this invention without departing from the spirit or scope thereof. For example:

Test system 100 may be implemented at least in part by a hand-held computer. The hand-held computer may use a graphical screen as a stimulus output device 106, and may use a capacitive touch screen input, a button, a microphone, or other such mechanism as a response input device 110.

Calibrators according to various embodiments may serve other purposes in addition to calibrating a test delivery system. For example, calibrators may comprise user interface sensor(s) that allow them to operate as a general purpose input device (e.g. a mouse) for user interaction with a personal computer. In particular embodiments, such user interface sensors could include two-axis position sensor(s) for communicating positional navigation to the test system and one or more button sensors for communicating selection clicks to the test system.

It should be understood that one or more of determining calibration metrics 504, storing calibration metrics 508, correcting test results 509, and updating test system 506, may be performed by or coordinated by a centralized computational service in a distributed computing environment (e.g. data communicating over a network connection to a server).

Calibration of a test system 100 may be performed at various times including one or more of the following non-limiting examples: once prior to performing stimulus-response tests, once after performing stimulus-response tests, prior to every stimulus-response tests, periodically based on an elapsed time or number of stimulus-response tests conducted.

What is claimed is:

1. A method of using a calibration system to generate a latency estimate for calibrating a stimulus-response test system, wherein the method comprises:

[a] providing a calibration system comprising a stimulus sensor, a response actuator device, and a first set of one or more processors;

[b] providing a stimulus-response test system comprising a stimulus output device for delivering stimuli to a subject, a response input device for receiving responses to the stimuli, a second set of one or more processors, and a response input interface for interfacing between the response input device and the second set of processors;

[c] sensing, using the stimulus sensor, a stimulus output event, the stimulus output event being indicative of delivery of stimulus by the stimulus output device to a subject;

[d] recording, using one or more of the first and second set of processors, a stimulus time associated with sensing the stimulus output event;

[e] generating, by one or more of the first and second set of processors, a calibrator response after sensing the stimulus output event, wherein generating the calibrator response comprises:
sending a response actuation signal from the first set of processors to the response actuator device, thereby causing the response actuator device to physically actuate the response input device via mechanical action, and thereby causing the response input device to provide a response input signal to the response input interface;

[f] recording, using one or more of the first and second set of processors, a response time associated with generating the calibrator response;

[g] determining, using one or more of the first and second set of processors, a calibrator delay ($t_{stim/tresp}$) based on a difference between the stimulus and response times;

[h] receiving a test system delay ($t_{tot}$) at one or more of the first and second set of processors, the test system delay representing a time difference between generating the stimulus at the test system and recording the response at the test system; and

[i] determining, using one or more of the first and second set of processors, a latency value ($t_{lat}$) based on a difference between the test system delay ($t_{tot}$) and the calibrator delay ($t_{stim/resp}$).

2. A method according to claim 1 further comprising:
recording a test-system stimulus time, the test-system stimulus time being associated with when at least one of the second set of processors outputs a signal causing the stimulus output device to deliver stimulus; and
recording a test-system response time, the test-system response time being associated with when at least one of the second set of processors receives the response input signal from the response input interface;
wherein receiving the test system delay $t_{tot}$ comprises determining a difference between the test-system response time and the test-system stimulus time.

3. A method according to claim 1 comprising:
[j] delaying for a delay period after sensing the stimulus output event in step [c] but before generating the calibrator response in step [e].

4. A method according to claim 1 further comprising:
[k] determining a plurality of latency values $t_{lat}$ by repeating steps [c] through [i] a plurality of times such that for each repetition of steps [c] through [i] a corresponding latency value $t_{lat}$ is determined; and
[l] determining a statistically expected latency value $E[t_{lat}]$ based at least in part on the determined plurality of latency values $t_{lat}$.

5. A method according to claim 3 further comprising:
[k] determining a plurality of latency values $t_{lat}$ by repeating steps [c] through [j] a plurality of times such that for each repetition of steps [c] through [j] a corresponding latency value $t_{lat}$ is determined; and
[l] determining a statistically expected latency value $E[t_{lat}]$ based at least in part on the determined plurality of latency values $t_{lat}$.

6. A method according to claim 5 wherein delaying for the delay period after sensing the stimulus output event but before generating the calibrator response comprises at least one of:
delaying for a constant delay period in each repetition of steps [c] through [j];
delaying for a random delay period from a probability distribution in each repetition of steps [c] through [j];
delaying for a sequentially increasing delay period in each sequential repetition of steps [c] through [j]; and
delaying for a sequentially decreasing delay period in each sequential repetition of steps [c] through [j].

7. A method according to claim 4 further comprising:
[m] determining a parameter indicative of the variability of the determined plurality of latency values $t_{lat}$.

8. A method according to claim 7 wherein the determined parameter indicative of the variability of the determined plurality of latency values $t_{lat}$ is based at least in part on a standard deviation of the determined plurality of latency values $t_{lat}$.

9. A method according to claim 7 wherein the determined parameter indicative of the variability of the determined plurality of latency values $t_{lat}$ is based at least in part on the range of the plurality of latency values $t_{lat}$, where the range is determined by a difference between a maximum and a minimum of the plurality of latency values $t_{lat}$.

10. A method according to claim 4 further comprising:
[k] communicating the statistically expected latency value $E[t_{lat}]$ to at least one processor of the second set of processors.

11. A method of using a calibration system to calibrate a stimulus-response test system, wherein the method comprises:
[a] providing a calibration system comprising a stimulus sensor, a response actuator device, and a first set of one or more processors;
[b] providing a stimulus-response test system comprising a stimulus output device for delivering stimuli to a subject, a response input device for receiving responses to the stimuli, a second set of one or more processors, and a response input interface for interfacing between the response input device and the second set of processors;
[c] sensing, using the stimulus sensor, a stimulus output event, the stimulus output event being indicative of delivery of stimulus by the stimulus output device to a subject;
[d] recording, using one or more of the first and second set of processors, a stimulus time associated with sensing the stimulus output event;
[e] generating, by one or more of the first and second set of processors, a calibrator response after sensing the stimulus output event, wherein generating the calibrator response comprises:
sending a response actuation signal from the first set of processors to the response actuator device, thereby causing the response actuator device to physically actuate the response input device via mechanical action, and thereby causing the response input device to provide a response input signal to the response input interface;
[f] recording, using one or more of the first and second set of processors, a response time associated with generating the calibrator response;

[g] determining, using one or more of the first and second set of processors, a calibrator delay ($t_{stim/tresp}$) based on a difference between the stimulus and response times;

[h] receiving a test system delay ($t_{tot}$) at one or more of the first and second set of processors, the test system delay representing a time difference between generating the stimulus at the test system and recording the response at the test system;

[i] determining, using one or more of the first and second set of processors, a latency value ($t_{lat}$) based on a difference between the test system delay ($t_{tot}$) and the calibrator delay ($t_{stim/resp}$); and

[j] using the latency value ($t_{lat}$) to calibrate one or more response times detected by the stimulus-response test system.

12. A method according to claim 11 wherein using the latency value ($t_{lat}$) to calibrate one or more response times detected by the stimulus-response test system comprises subtracting the latency value ($t_{lat}$) from at least one of the one or more response times.

* * * * *